US012653519B2

(12) United States Patent
Yamanaka et al.

(10) Patent No.: US 12,653,519 B2
(45) Date of Patent: Jun. 16, 2026

(54) SUTURE ANCHOR AND LACERATION REPAIR DEVICE

(71) Applicant: OLYMPUS CORPORATION, Tokyo (JP)

(72) Inventors: Noriaki Yamanaka, Tokyo (JP); Masahiro Fujii, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 497 days.

(21) Appl. No.: 18/158,764

(22) Filed: Jan. 24, 2023

(65) Prior Publication Data

US 2023/0157682 A1 May 25, 2023

Related U.S. Application Data

(63) Continuation of application No. PCT/JP2020/030384, filed on Aug. 7, 2020.

(51) Int. Cl.
*A61B 17/04* (2006.01)

(52) U.S. Cl.
CPC .. *A61B 17/0401* (2013.01); *A61B 2017/0406* (2013.01); *A61B 2017/0409* (2013.01); (Continued)

(58) Field of Classification Search
CPC ........ A61B 17/0401; A61B 2017/0409; A61B 2017/0414; A61B 2017/042; (Continued)

(56) References Cited

U.S. PATENT DOCUMENTS 5,078,731 A 1/1992 Hayhurst
5,693,060 A * 12/1997 Martin ............. A61B 17/12013
606/148

(Continued)

FOREIGN PATENT DOCUMENTS

EP 2215972 A1 8/2010
EP 2215973 A1 8/2010

(Continued)

OTHER PUBLICATIONS

"International Application Serial No. PCT/JP2020/030384, International Search Report dated Oct. 27, 2020", w/ English Translation, (Oct. 27, 2020), 5 pgs.

*Primary Examiner* — Jing Rui Ou
(74) *Attorney, Agent, or Firm* — Schwegman Lundberg & Woessner, P.A.

(57) ABSTRACT

A suture anchor including a base, a deformable portion, and a first passage and a second passage each formed in the base to allow a suture to pass therethrough, wherein the deformable portion is a cantilever state having a fixed end, which is disposed at a side of one end of the base, and a free end, which is disposed at a side of the other end of the base relative to the fixed end and which is separated by a space from the base, and the deformable portion is deformable in a direction in which the free end approaches the base, the first passage communicates the upper side and the lower side of the base, the second passage communicates the space and a side of the one end of the fixed end, and the deformable portion is deformed due to a tensile force applied to the suture.

11 Claims, 23 Drawing Sheets

(52) U.S. Cl.
CPC . *A61B 2017/0414* (2013.01); *A61B 2017/042* (2013.01); *A61B 2017/0458* (2013.01); *A61B 2017/0459* (2013.01); *A61B 2017/0464* (2013.01)

(58) Field of Classification Search
CPC .... A61B 2017/0464; A61B 2017/0458; A61B 2017/0406; A61B 2017/0459
See application file for complete search history.

(56) References Cited

U.S. PATENT DOCUMENTS

| | | | |
|---|---|---|---|
| 7,150,757 B2 * | 12/2006 | Fallin | A61B 17/0487 |
| | | | 606/103 |
| 7,722,644 B2 * | 5/2010 | Fallin | A61B 17/0487 |
| | | | 606/103 |
| 10,085,740 B1 * | 10/2018 | Anderson | A61B 17/0401 |
| 2002/0019649 A1 | 2/2002 | Sikora et al. | |
| 2002/0173788 A1 * | 11/2002 | Bojarski | A61B 17/0401 |
| | | | 606/60 |
| 2003/0130694 A1 | 7/2003 | Bojarski et al. | |
| 2004/0254593 A1 | 12/2004 | Fallin et al. | |
| 2005/0033363 A1 | 2/2005 | Bojarski et al. | |
| 2005/0283192 A1 | 12/2005 | Torrie et al. | |
| 2010/0114161 A1 | 5/2010 | Bojarski et al. | |
| 2010/0114162 A1 | 5/2010 | Bojarski et al. | |
| 2010/0121348 A1 * | 5/2010 | van der Burg | A61B 17/888 |
| | | | 606/232 |
| 2010/0204731 A1 | 8/2010 | Hart et al. | |
| 2012/0016386 A1 | 1/2012 | Bojarski et al. | |
| 2013/0096613 A1 | 4/2013 | Hart et al. | |
| 2013/0103085 A1 | 4/2013 | Hart et al. | |
| 2013/0144314 A1 | 6/2013 | Bojarski et al. | |
| 2013/0310874 A1 | 11/2013 | Torrie et al. | |
| 2014/0350599 A1 | 11/2014 | Torrie et al. | |
| 2015/0066060 A1 | 3/2015 | Bojarski et al. | |
| 2017/0231619 A1 | 8/2017 | Bojarski et al. | |
| 2019/0150914 A1 | 5/2019 | Bojarski et al. | |

FOREIGN PATENT DOCUMENTS

| | | |
|---|---|---|
| JP | 07500974 A | 2/1995 |
| JP | 4160386 B2 | 10/2008 |
| JP | 2010179102 A | 8/2010 |
| WO | WO-9309717 A1 | 5/1993 |
| WO | WO-0236020 A1 | 5/2002 |
| WO | WO-2005000100 A2 | 1/2005 |

* cited by examiner

START

ATTACH FIRST ANCHOR AND
SECOND ANCHOR TO SUTURE ～S1

LOAD FIRST ANCHOR AND SECOND
ANCHOR INTO DELIVERY DEVICE ～S2

INSERT DELIVERY DEVICE
INTO KNEE JOINT ～S3

DISPOSE FIRST ANCHOR AT TISSUE ～S4

DISPOSE SECOND ANCHOR AT TISSUE ～S5

PULL FREE-END PORTION OF SUTURE ～S6

CUT SUTURE ～S7

REMOVE DELIVERY DEVICE
FROM THE INTERIOR OF KNEE JOINT ～S8

END

SUTURE ANCHOR AND LACERATION REPAIR DEVICE

CROSS-REFERENCE TO RELATED APPLICATIONS

This is a continuation of International Application PCT/JP2020/030384, with an international filing date of Aug. 7, 2020, which is hereby incorporated by reference herein in its entirety.

TECHNICAL FIELD

The present invention relates to a suture anchor and a laceration repair device.

BACKGROUND ART

In the related art, there are a known device and method for repairing a wound in tissue such as a knee joint meniscus (for example, see PTL 1). The device of PTL 1 includes a first securing member, a second securing member, and a suture connected to the first securing member and the second securing member. The suture is secured to the first securing member and is movable with respect to the second securing member. The first securing member and the second securing member pass through the tissue and are disposed on a surface of the tissue so that a portion of the suture between the first securing member and the second securing member crosses the wound, the suture is subsequently pulled, and thus, the wound is closed.

CITATION LIST

Patent Literature

{PTL 1} Publication of Japanese Patent No. 4160386

SUMMARY

An aspect of the present invention is a suture anchor including: a plate-like base that has an upper side and a lower side in a thickness direction of the base and that has one end and the other end in a direction intersecting the thickness direction; a deformable portion disposed at an upper side of the base, at least a side of the other end of the deformable portion being disposed so as to be separated by a space from the base; and a first passage and a second passage each formed in the base to allow a suture to pass therethrough, wherein the deformable portion is a cantilever state having a fixed end, which is disposed at a side of the one end and fixed to the base, and a free end, which is disposed at a side of the other end, and the deformable portion is deformable in a direction in which the free end approaches the base, the first passage communicates the upper side and the lower side of the base, the second passage is formed on a side of the one end relative to the free end and the first passage and communicates the space and a side of the one end of the fixed end, and the deformable portion is deformed due to a tensile force applied to the suture, which extends from the first passage and returns to the first passage via a side of the other end relative to the deformable portion, an opposite side of the deformable portion when seen from the base, a side of the one end relative to the deformable portion, the second passage, and the space, and to hold the suture between the deformable portion and the base.

3

Figure 14A:
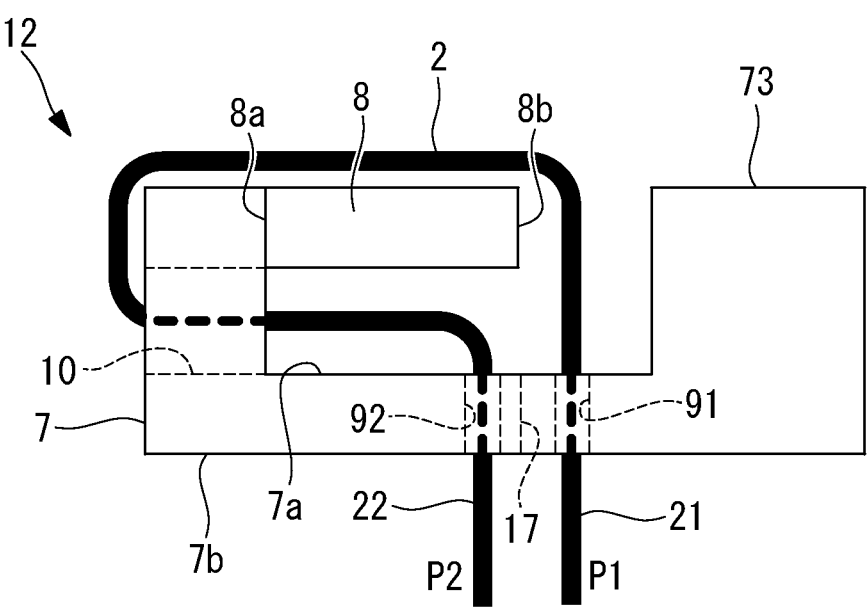

FIG. 14A is a side view of another modification of the second anchor provided with a groove in an inner surface of a first passage.

Figure 14B:
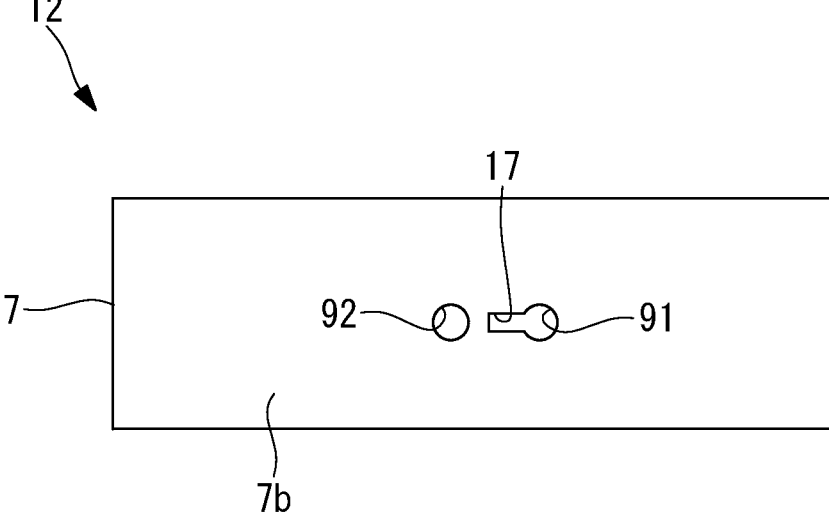

FIG. 14B is a bottom view of the second anchor in FIG. 14A.

Figure 15:
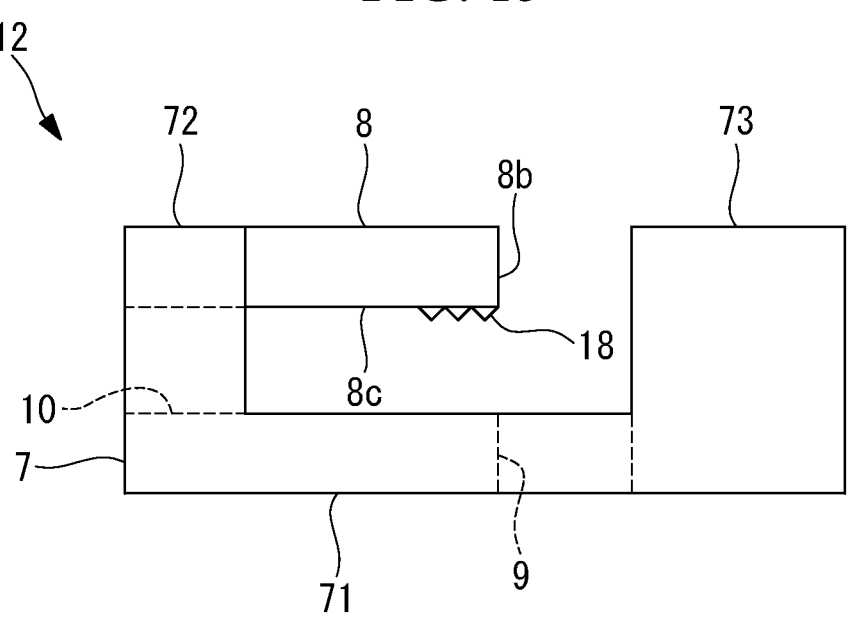

FIG. 15 is a side view of another modification of the second anchor provided with protrusions.

Figure 16A:
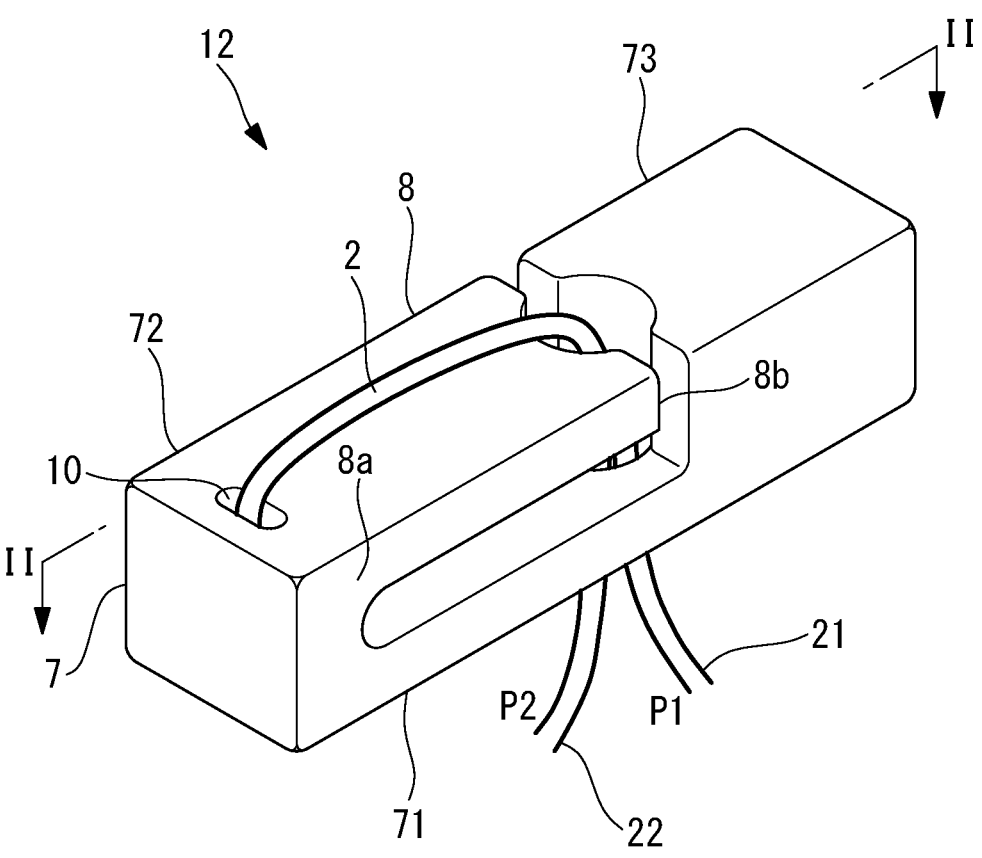

FIG. 16A is a perspective view of a top surface of another modification of the second anchor.

Figure 16B:
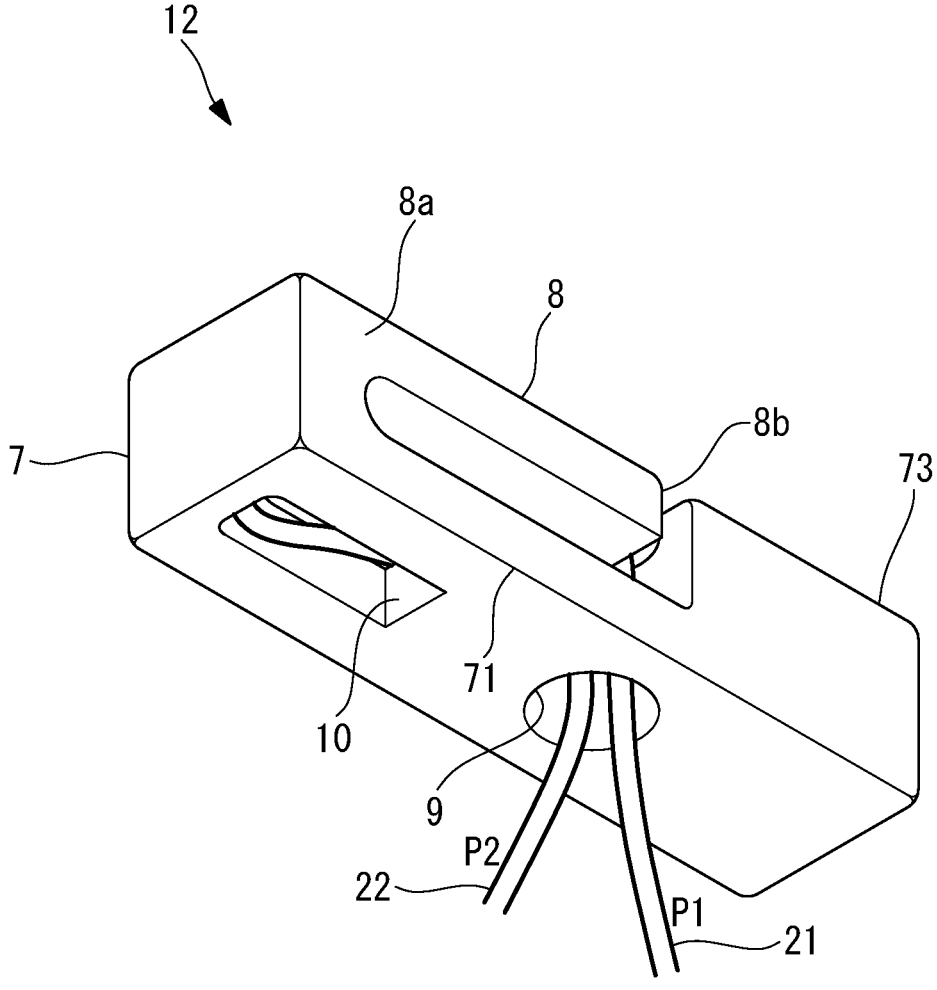

FIG. 16B is a perspective view of a bottom surface of the suture anchor in FIG. 16A.

Figure 16C:
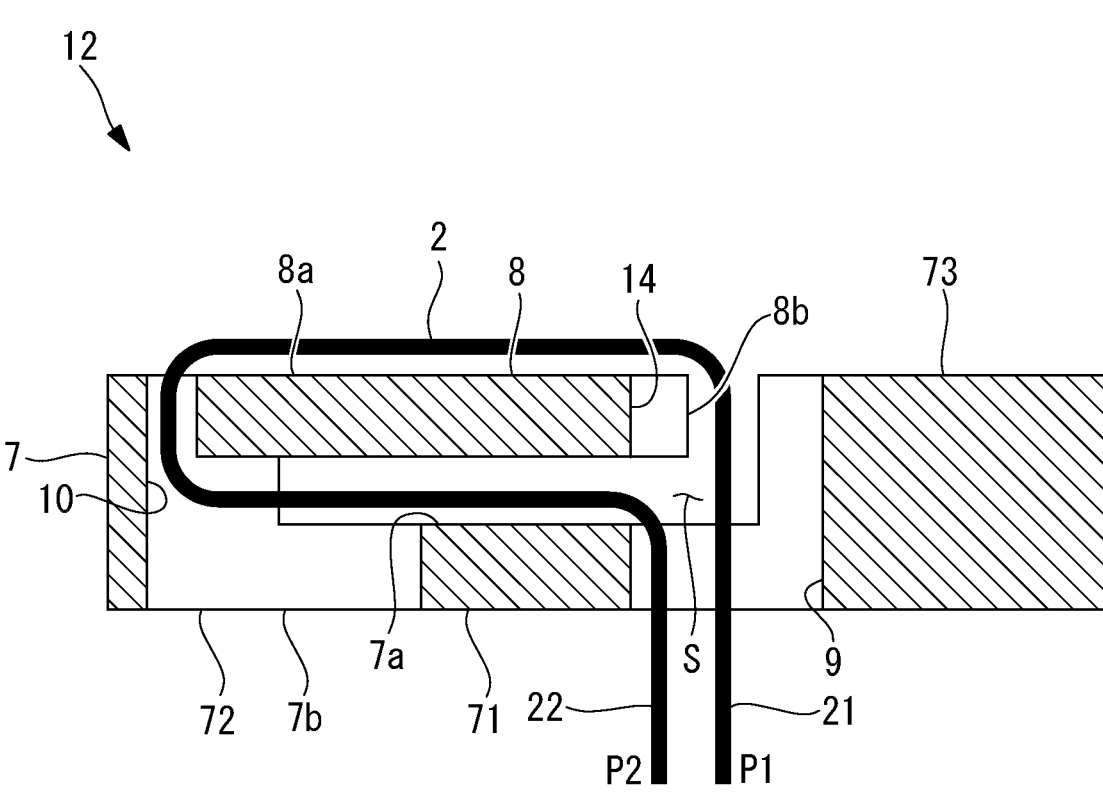

FIG. 16C is a longitudinal sectional view of the suture anchor in FIG. 16A taken along II-II.

Figure 17:
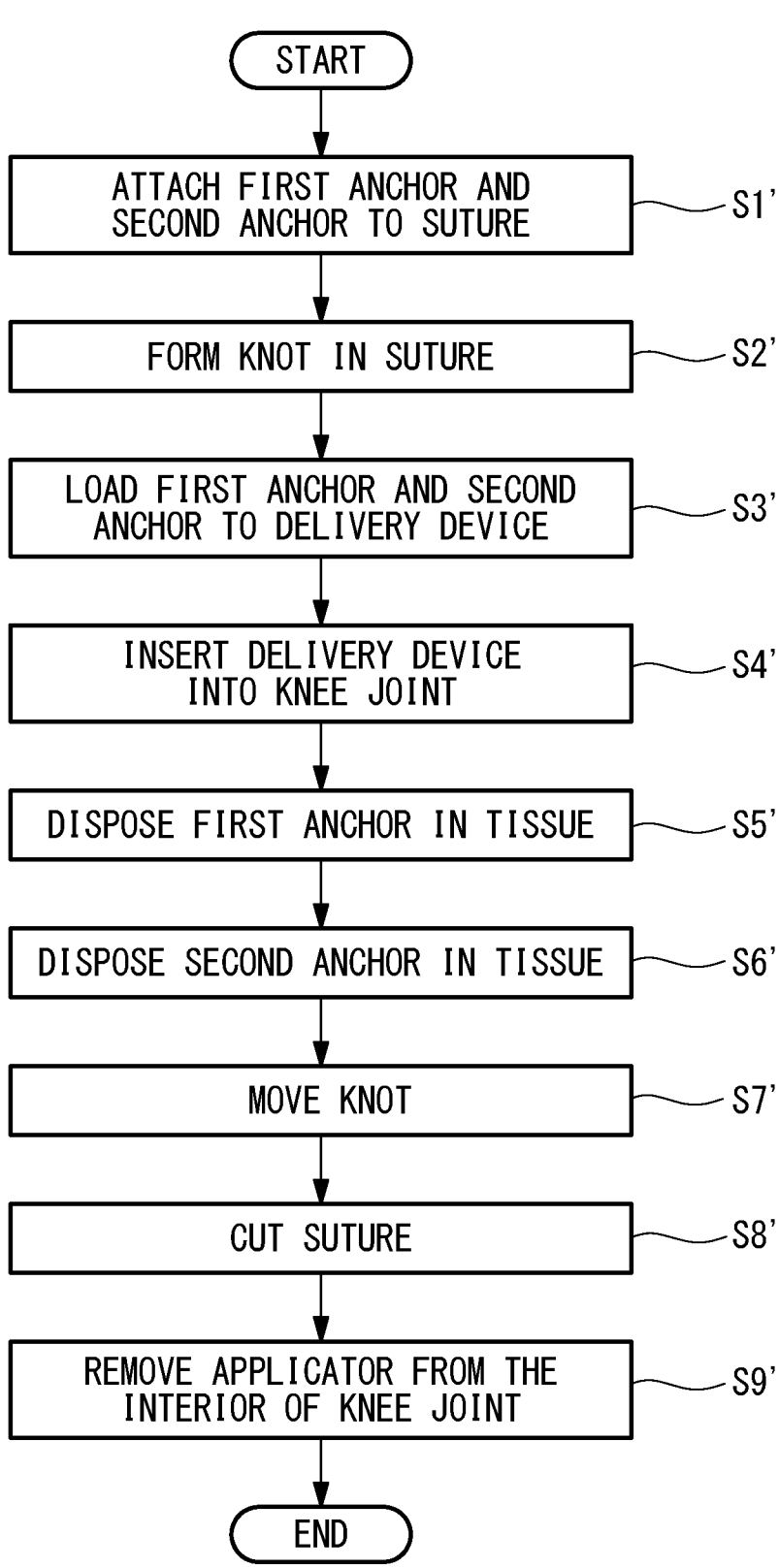

FIG. 17 is a flowchart showing a laceration repair method according to a comparative example.

DESCRIPTION OF EMBODIMENTS

A suture anchor and a laceration repair device according to an embodiment of the present invention will be described below with reference to the drawings.

Figure 1:
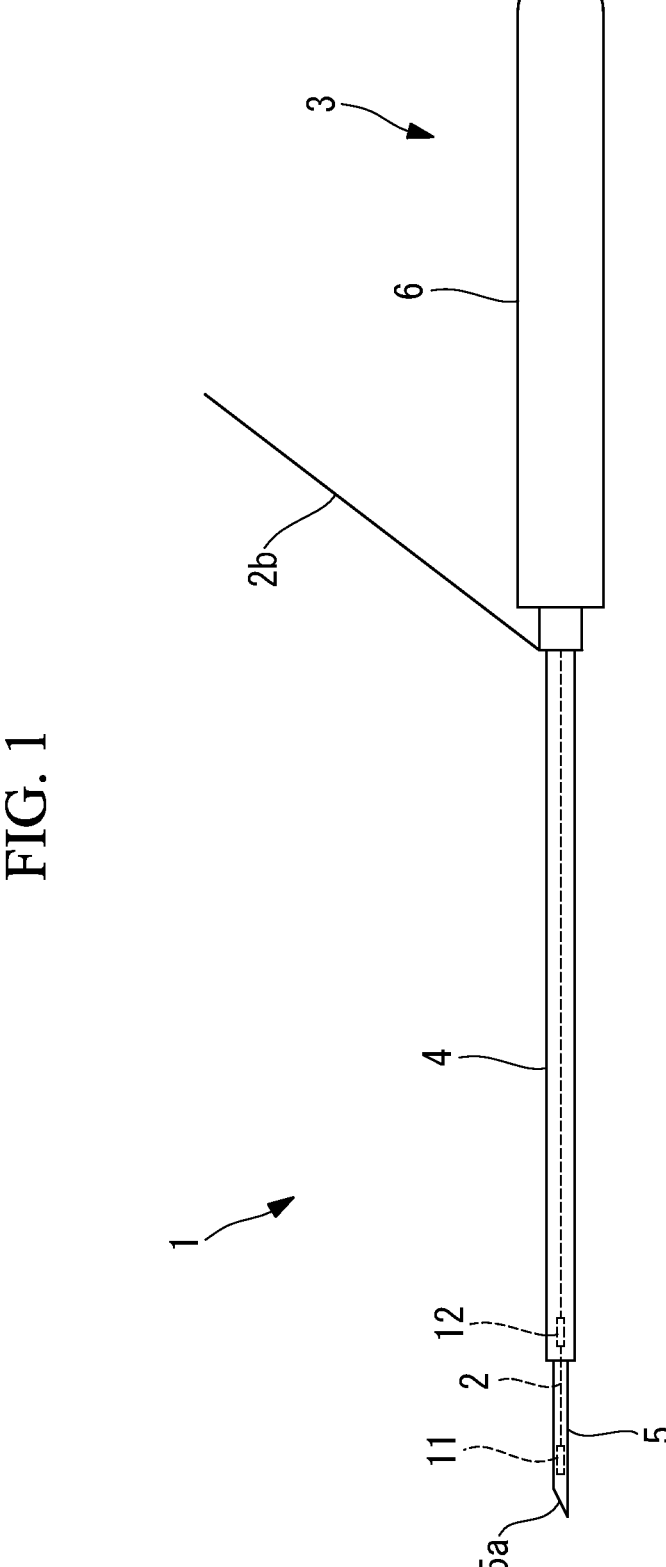
FIG. 1 is a configuration diagram showing, in outline, a laceration repair device according to an embodiment of the present invention.

A laceration repair device 1 according to this embodiment is used in laceration repair surgery in which a laceration in soft tissue is sutured by means of a suture 2 to repair the laceration. As shown in FIG. 1, the laceration repair device 1 includes a first anchor 11, a second anchor 12, the suture 2, and a delivery device 3.

Figure 2:
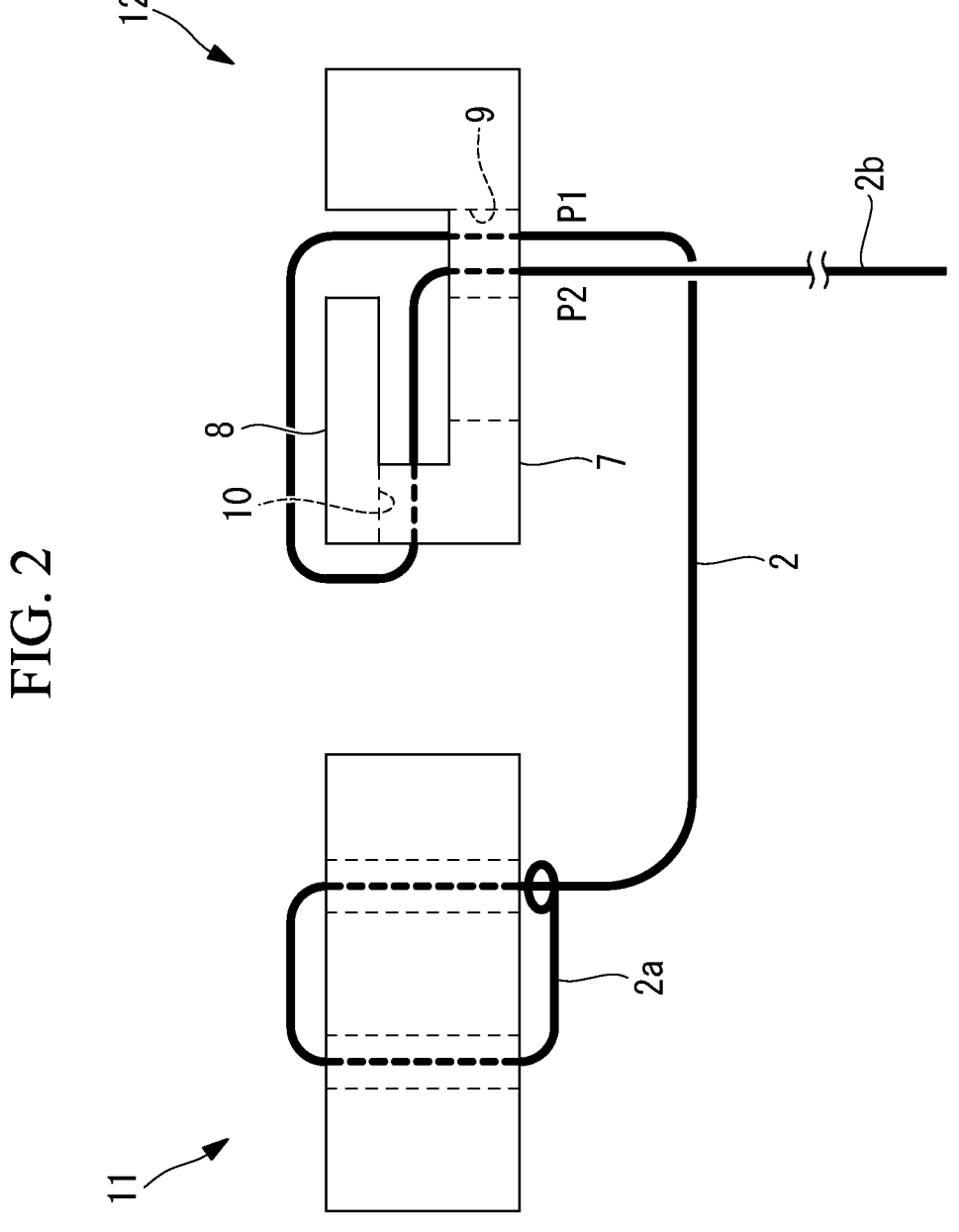
FIG. 2 is a configuration diagram showing, in outline, a first anchor and a second anchor included in the laceration repair device in FIG. 1.

As shown in FIG. 2, the anchors 11 and 12 are attached to the suture 2 and secure the suture 2 to soft tissue so that the suture 2 made to pass through the soft tissue is not removed. The first anchor 11 is secured to a secured end portion 2a, which is one end portion of the suture 2, and is disposed on the soft tissue first in the laceration repair surgery. The second anchor 12 is attached to the suture 2 so as to be movable with respect to the suture 2 at a position between the first anchor 11 and a free end portion 2b, which is the other end portion of the suture 2, and is disposed on the soft tissue second in the laceration repair surgery. The suture anchor according to the present invention is used as the second anchor 12. The first anchor 11 is an arbitrary anchor for the suture and may be the suture anchor according to the present invention.

The suture 2 is an arbitrary flexible suture that is generally used in suturing soft tissue and is, for example, a suture of size 2.0.

The delivery device 3 delivers the anchors 11 and 12 to a surface of the soft tissue via the interior of the soft tissue. The delivery device 3 includes a circular tube-like sheath 4, an elongated hollow needle 5 having a needle tip 5a at a distal end thereof, and a handle 6 connected to a proximal end of the sheath 4. The needle 5 is accommodated in the sheath 4, a proximal end of the needle 5 is connected to the handle 6, and a distal-end portion of the needle 5, including the needle tip 5a, protrudes from a distal end of the sheath 4.

The anchors 11 and 12 are loaded into the interior of the needle 5 and are arrayed in the longitudinal direction of the needle 5. The first anchor 11 is disposed on a distal side of the needle 5, and the second anchor 12 is disposed on a proximal side of the needle 5. A side wall of the needle 5 may be provided with a slit that extends toward a proximal end side from the needle tip 5a and that extends through the side wall in the radial direction, and the anchors 11 and 12 may be configured so as to be movable along the slit. The suture 2 connected to the anchors 11 and 12 pass through the sheath 4 and are pulled out to the outside from the proximal end of the sheath 4.

An actuator (not shown) for sequentially pushing out the anchors 11 and 12 one at a time from the needle tip 5a is provided in the interior of the delivery device 3. For example, a user can actuate the actuator, for example, by operating an operating member (not shown), such as a slider, provided in the handle 6 to make the first anchor 11 and the second anchor 12 sequentially protrude from the needle tip 5a.

In the example in FIG. 2, the first anchor 11 made of a plate-like member and is provided with two holes that respectively extend through the first anchor 11 in a thickness direction thereof. The first anchor 11 is formed of, for example, a resin such as PEEK (polyether ether ketone).

Figure 3A:
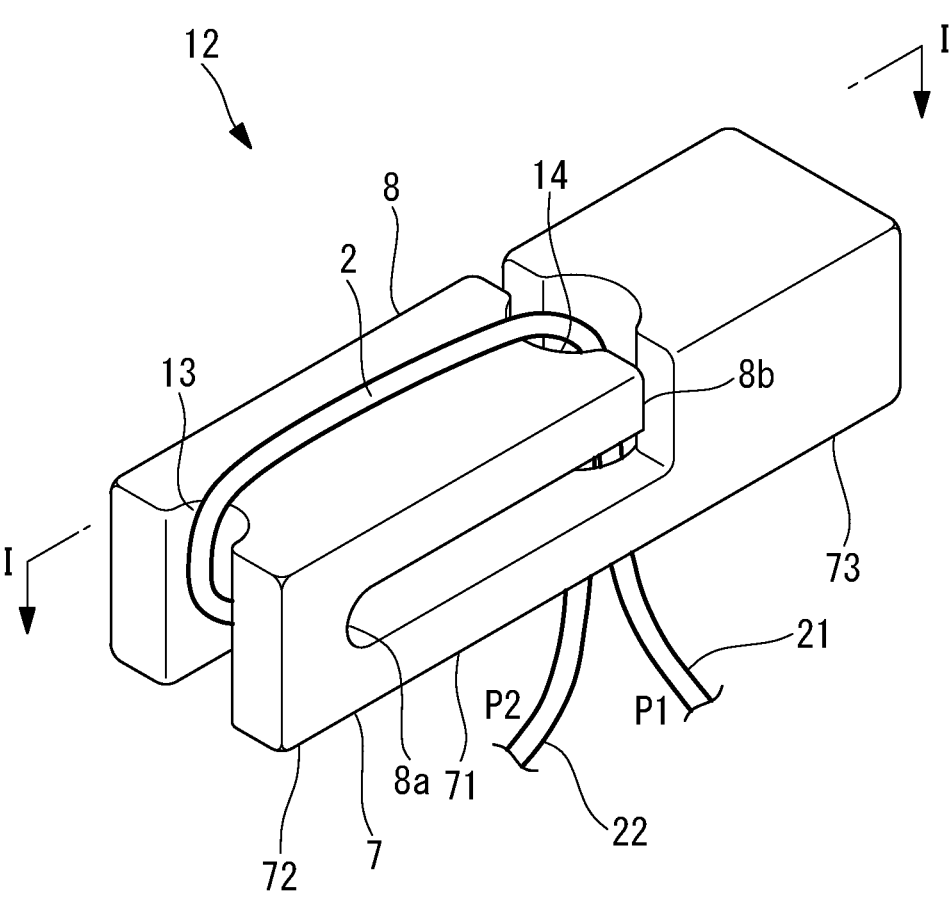
FIG. 3A is a perspective view of a top surface of a suture anchor according to this embodiment.
Figure 3B:
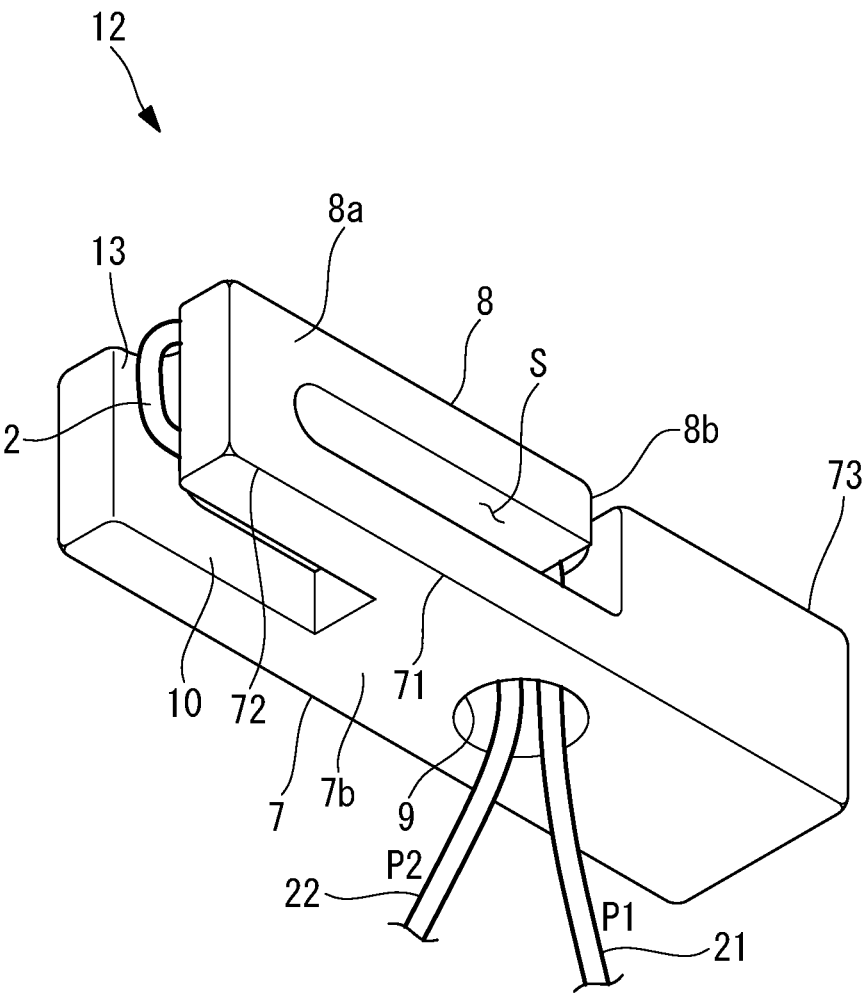
FIG. 3B is a perspective view of a bottom surface of the suture anchor in FIG. 3A.

As shown in FIGS. 3A and 3B, the suture anchor 12, which is the second anchor, includes a base 7, a deformable portion 8, and two passages 9 and 10 through which the suture 2 passes. At least the deformable portion 8 of the suture anchor 12 is formed of an elastically deformable material, for example, a resin such as PEEK (polyether ether ketone). The base 7 and the deformable portion 8 are, for example, integrally molded using the same material.

Figure 4A:
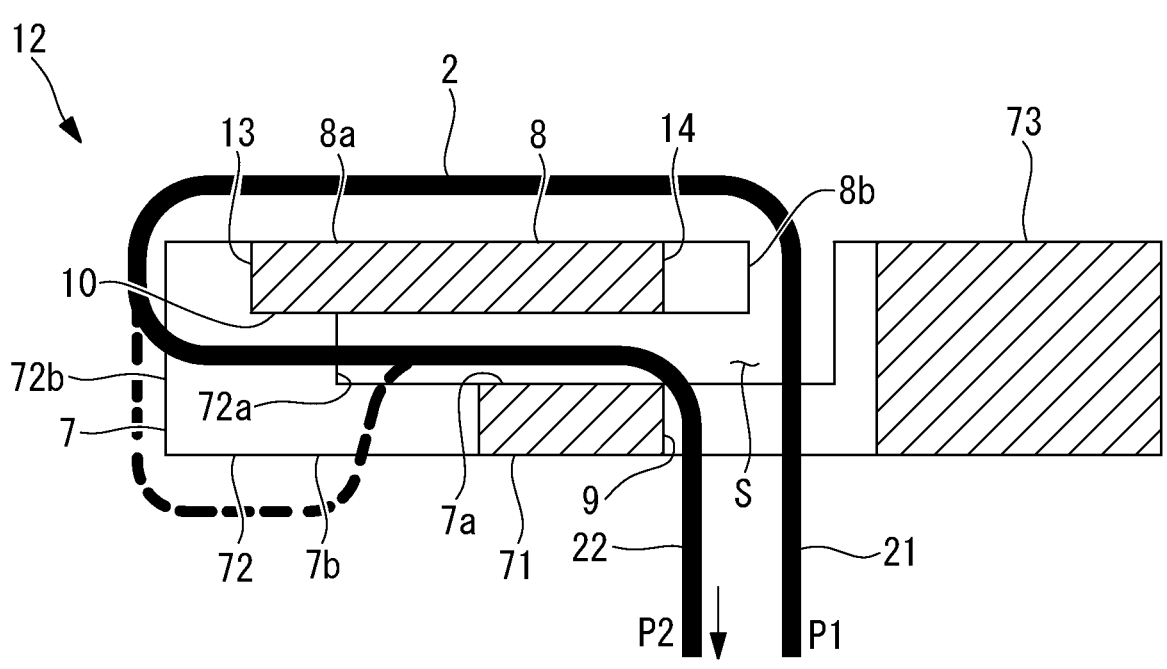
FIG. 4A is a longitudinal sectional view of the anchor in FIG. 3A taken along I-I in a state in which a deformable portion is not deformed.
Figure 4B:
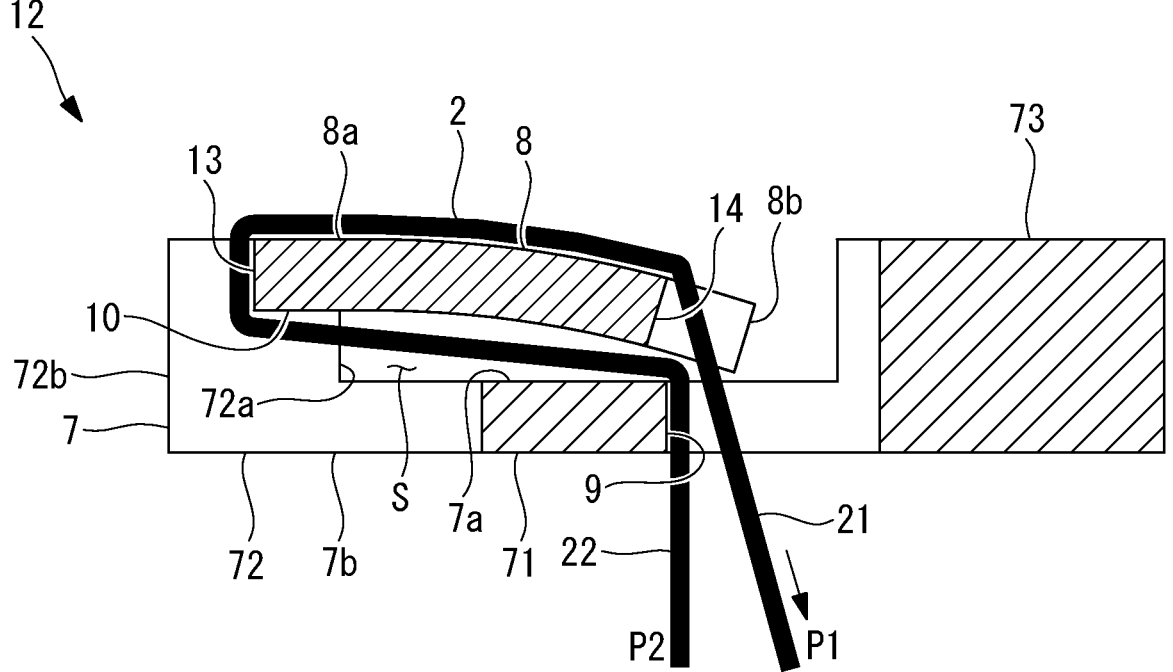
FIG. 4B is a longitudinal sectional view of the anchor in FIG. 3A taken along I-I in a state in which the deformable portion is deformed.
Figure 5A:
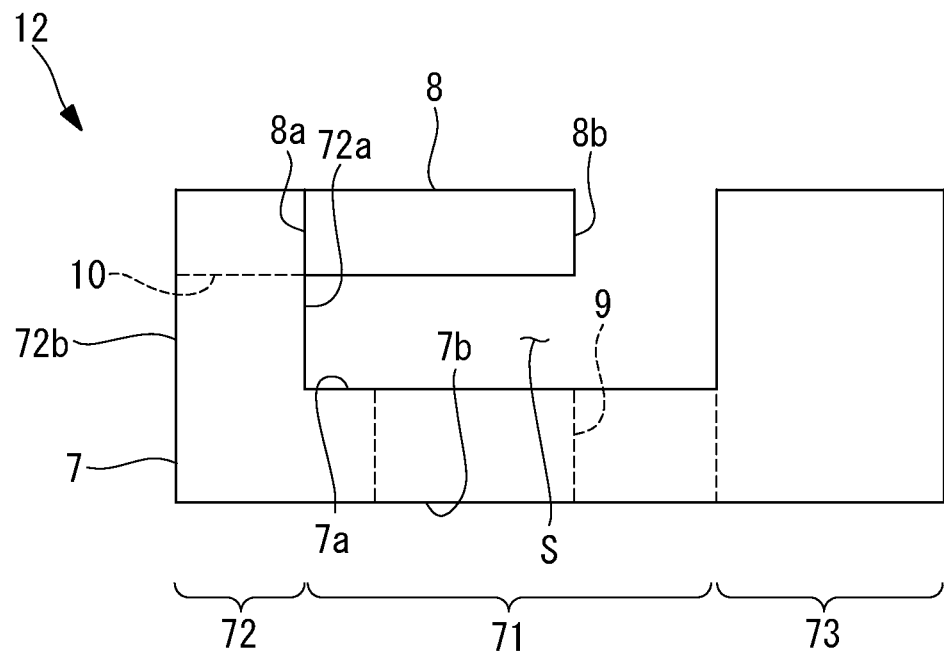
FIG. 5A is a simplified side view of the anchor in FIG. 3A in the state in which the deformable portion is not deformed.
Figure 5B:
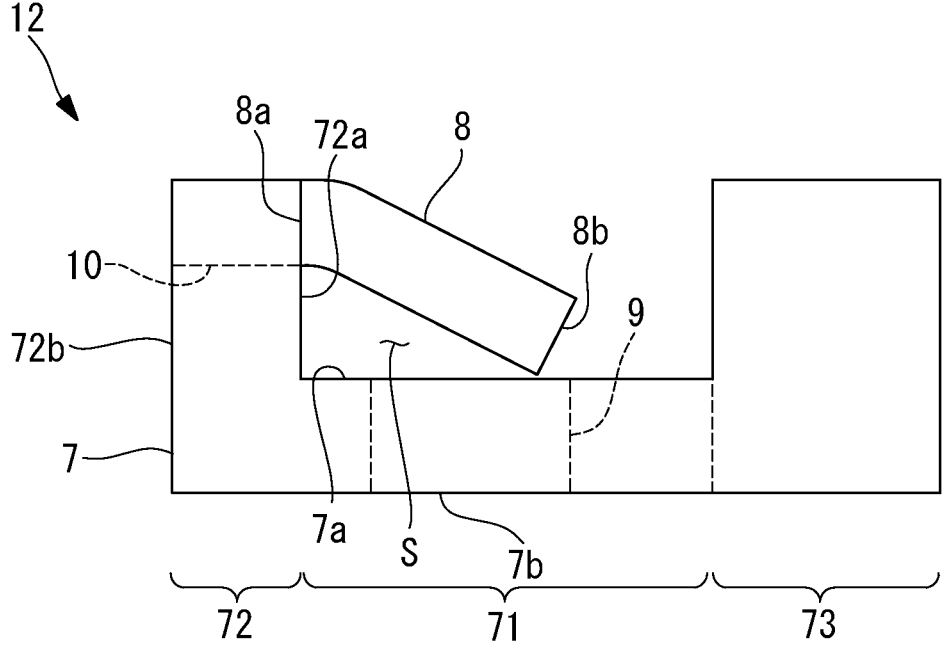
FIG. 5B is a simplified side view of the anchor in FIG. 3A in the state in which the deformable portion is deformed.

As will be described later, the deformable portion 8 deforms due to a tensile force of the suture 2 and the suture anchor 12 secures the suture 2 so that the suture 2 does not move with respect to the suture anchor 12 by holding the suture 2 between the base 7 and the deformed deformable portion 8. FIGS. 4A and 5A show a state in which the deformable portion 8 is not deformed and FIGS. 4B and 5B show a state in which the deformable portion 8 is deformed. FIGS. 4A and 4B are sectional views of the suture anchor 12 and FIGS. 5A and 5B are simplified side views of the suture anchor 12.

The base 7 is a plate-like member and has a rectangular shape having a longitudinal direction and a transverse direction in a plan view or a bottom view viewed in the thickness direction thereof. The base 7 has an upper side and a lower side in the thickness direction and has one end side and the other end side in the longitudinal direction intersecting the thickness direction. The upper side, the lower side, the one end side, and the other end side of the base 7 respectively correspond to an upper side, a lower side, one end side, and the other end side of the suture anchor 12, and, in the drawings to which reference is made, the left side is the one end side and the right side is the other end side.

In a side view viewed in the transverse direction, a bottom surface 7b of the base 7 is a flat surface and a top surface 7a of the base 7 is a stepped surface. Specifically, the base 7 at least has a thin portion 71 and a thick portion 72 that is adjacent to the thin portion 71 on the one end side thereof and that protrudes toward the upper side with respect to the thin portion 71. The base 7 may additionally have a thick end portion 73 that is adjacent to the thin portion 71 on the other end side thereof and that protrudes toward the upper side with respect to the thin portion 71.

The deformable portion 8 is a flat plate-like member that is disposed on the upper side of the base 7 so as to be substantially parallel to the base 7. The thin portion 71 and the deformable portion 8 of the base 7 face each other in the thickness direction and are separated by a space S through which the suture 2 passes. The deformable portion 8 has a cantilever state that protrudes toward the other end side from a side surface 72a of the thick portion 72 of the base 7 and has a secured end 8a that is disposed on the one end side and that is secured to the side surface 72a of the thick portion 72 and a free end 8b that is disposed on the other end side. Due to deflection deformation of the deformable portion 8, the free end 8b approaches the base 7. The suture 2 passes through the space S once. The dimension of the space S in the thickness direction is greater than the diameter of the suture 2, and the suture 2 in the space S is movable at least in the longitudinal direction of the base 7 with respect to the base 7.

The first passage 9 is a passage through which the suture 2 passes from the lower side of the base 7 to the upper side thereof and from the upper side to the lower side and that communicates the lower side and the upper side of the base 7. Specifically, the first passage (first hole) 9 is a hole that extends through the thin portion 71 of the base 7 in the thickness direction and opens in the top surface 7a and the bottom surface 7b. The suture 2 passes through the first passage 9 twice. At least in one radial direction of the first passage 9, the diameter of the first passage 9 is more than twice as large as the diameter of the suture 2, and the suture 2 in the first passage 9 is movable in the thickness direction with respect to the base 7. For example, the first passage 9 has an elliptical shape or an elongated circular shape having a long axis in the longitudinal direction of the base 7.

As will be described later, when attaching the suture anchor 12 to the suture 2, the free end portion 2b of the suture 2 is moved between the lower side of the base 7 and the upper side of the deformable portion 8 via the first passage 9 (see FIGS. 6C and 6D). In order to facilitate this work, it is preferable that at least a portion of the first passage 9 be formed on a side of the other end with respect to the free end 8b.

In addition, the first passage 9 may extend to the one end side from the other end side with respect to the free end portion 2b so that the suture 2 is held at an angular portion between an inner surface of the first passage 9 and a top surface 7a of the thin portion 71 when the deformable portion 8 is deformed.

The second passage 10 is a passage through which the suture 2 passes into the space S from the one end side of the secured end 8a, is formed on the one end side with respect to the free end 8b and the first passage 9, and communicates the space S and the one end side of the secured end 8a. The suture 2 passes through the second passage 10 once. The diameter of the second passage 10 is greater than the diameter of the suture 2 and the suture 2 in the second passage 10 is movable at least in the longitudinal direction of the base 7 with respect to the base 7.

Specifically, as shown in FIGS. 3B to 4B, the second passage (second hole) 10 is a hole that extends through the thick portion 72 of the base 7 in the longitudinal direction of the base 7 and that extends through one end portion of the thin portion 71 in the thickness direction. One of the openings of the second passage 10 is formed in a side surface 72b on the one end side of the thick portion 72 and the bottom surface 7b and is a large opening that is continuous between the side surface 72b and the bottom surface 7b. The other opening of the second passage 10 is formed in the side surface 72a on the other end side of the thick portion 72 and the top surface 7a of the thin portion 71 and is an opening that is continuous between the side surface 72a and the top surface 7a.

FIGS. 6A to 6E describe a method for attaching the suture anchor 12 to the suture 2. The anchors 11 and 12 are attached to the suture 2 by a manufacturer, and the laceration repair device 1 is provided to a user in a state in which the anchors 11 and 12 are loaded in the delivery device 3.

In the case in which the laceration repair device 1 is provided to the user in a state in which the anchors 11 and 12, the suture 2, and the delivery device 3 are separated from each other, the user may attach the anchors 11 and 12 to the suture 2.

Figure 6A:
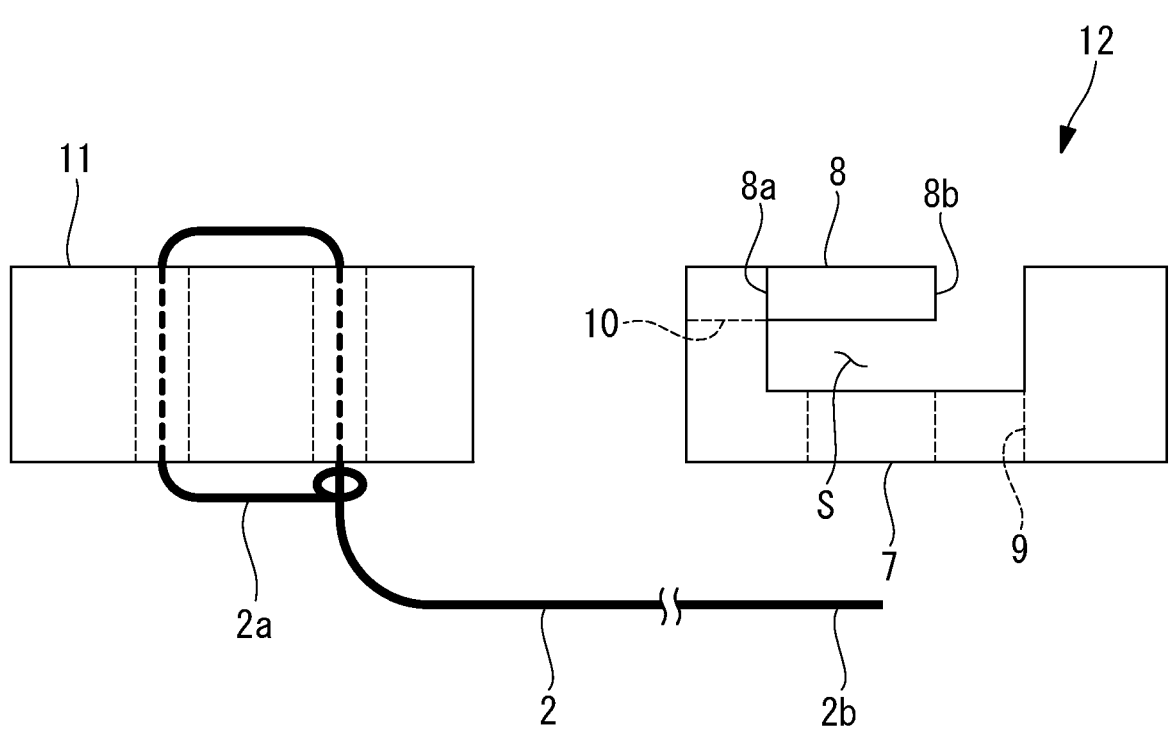
FIG. 6A is a diagram for explaining a method for attaching the second anchor to a suture.
Figure 6B:
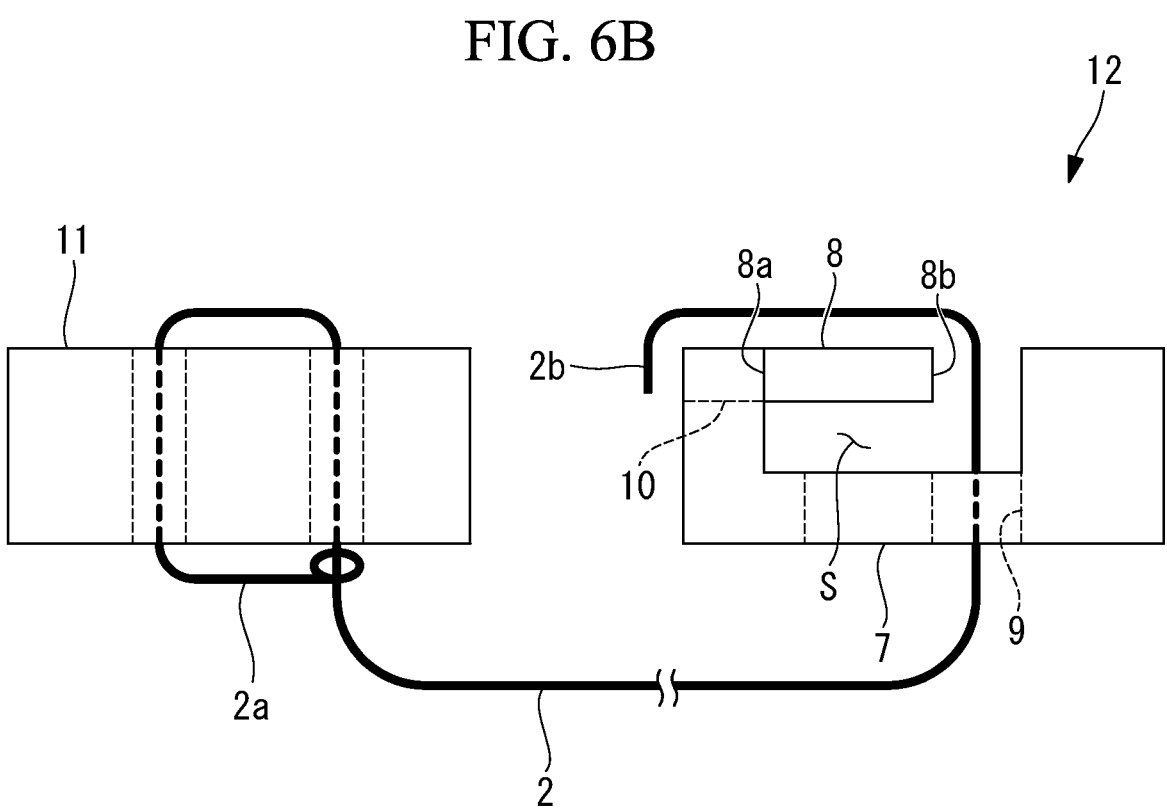
FIG. 6B is a diagram for explaining the method for attaching the second anchor to the suture.

As shown in FIG. 6A, the suture anchor 12 is attached to the suture 2 after attaching the first anchor 11 to the secured end portion 2a of the suture 2 by means of a publicly known method. As shown in FIG. 6B, the free end portion 2b of the suture 2 is made to pass through the first passage 9 from the lower side to the upper side and is moved to the one end side of the deformable portion 8 and the base 7 via the other end side and the upper side of the deformable portion 8.

Figures 6C, 6D:
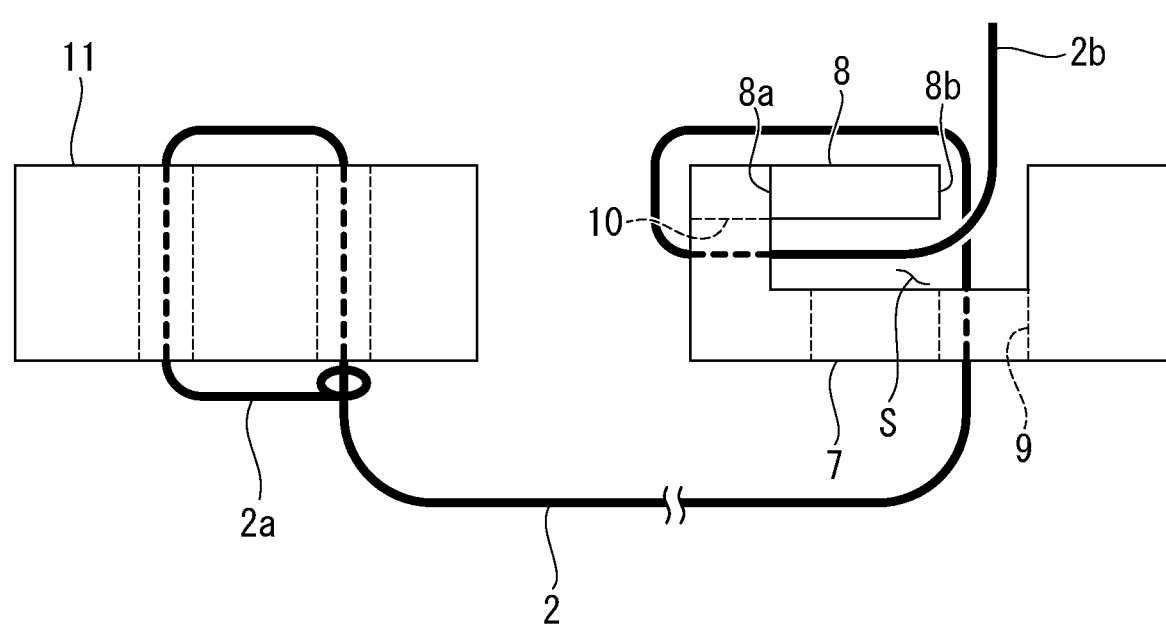
FIG. 6C is a diagram for explaining the method for attaching the second anchor to the suture.
FIG. 6D is a diagram for explaining the method for attaching the second anchor to the suture.

Next, as shown in FIG. 6C, the free end portion 2b is made to pass through the second passage 10 from the one end side to the other end side and is moved to the upper side of the deformable portion 8 via the space S and the other end side of the deformable portion 8. At this time, one of the openings of the second passage 10, which serves as the entrance for the suture 2, is the large opening that is continuous between the side surface 72a and the bottom surface 7b. Therefore, as respectively indicated by the solid line and the broken line in FIG. 4A, it is possible to easily make the suture 2 pass into the second passage 10 from the one end side or the lower side.

Figure 6E:
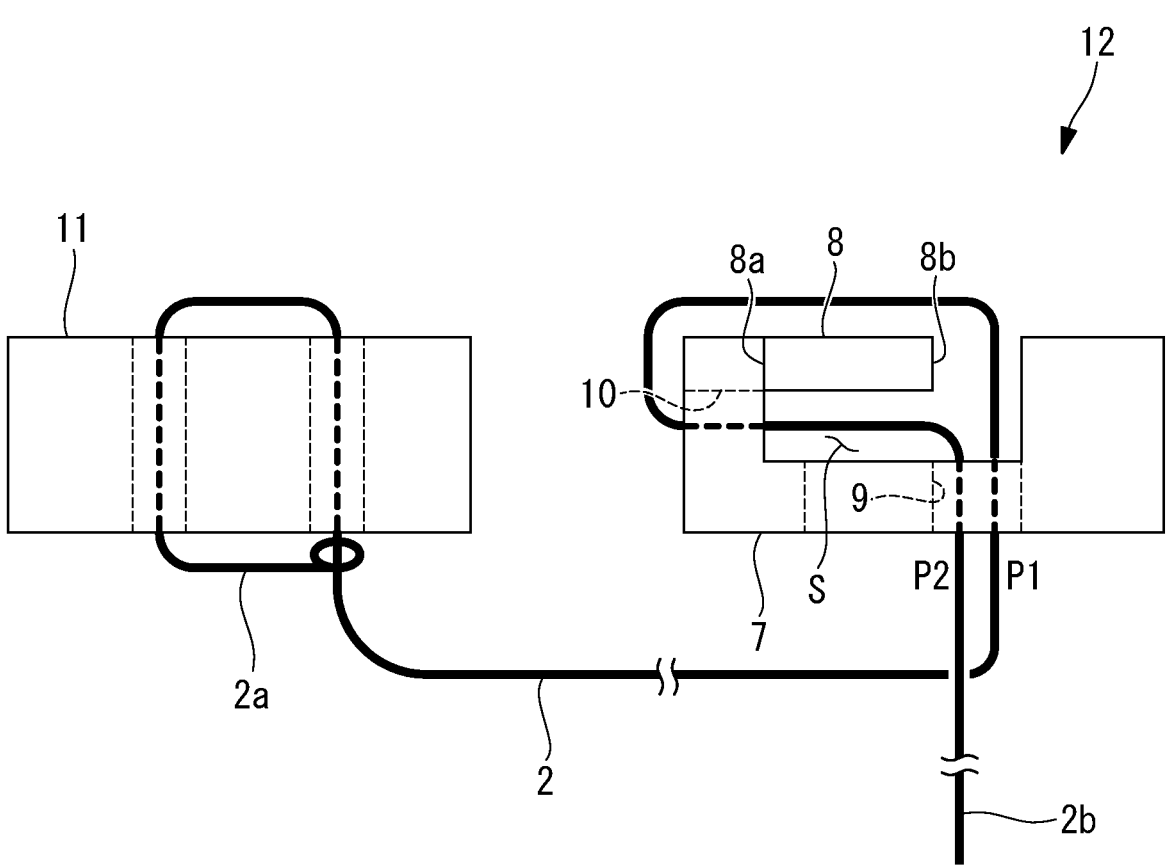
FIG. 6E is a diagram for explaining the method for attaching the second anchor to the suture.

Next, as shown in FIG. 6D, the free end portion 2b is moved to the lower side of the deformable portion 8 from the upper side thereof via the other end side of the deformable portion 8 and is made to pass through the first passage 9 from the upper side to the lower side. Next, as shown in FIG. 6E, the free end portion 2b is pulled and the excess length of the suture 2 between the second passage 10 and the first passage 9 is eliminated.

As a result of making the free end portion 2b of the suture 2 pass through the passages 9 and 10 in the above-described manner, the suture 2 extends from the first passage 9 via the other end side, the upper side, and the one end side of the deformable portion 8 and subsequently returns to the first passage 9 via the second passage 10 and the space S. Therefore, two portions 21 and 22 of the suture 2 pass through the first passage 9. The first portion 21 is a portion on the first anchor 11 side, extending along a first route P1 leading to the first anchor 11, and extends toward the upper side of the deformable portion 8 from the first passage 9 via the other end side of the deformable portion 8. The second portion 22 is a portion on the free end portion 2b side, extending along a second route P2 leading to the free end portion 2b, and extends toward the one end side of the deformable portion 8 from the first passage 9 via the space S and the second passage 10.

As shown in FIG. 4A, the suture 2 wound around the periphery of the deformable portion 8 in this way is movable with respect to the suture anchor 12 in accordance with a pulling force when the second portion 22 in the second route P2 is pulled. On the other hand, as shown in FIG. 4B, the suture 2 cannot be moved with respect to the suture anchor 12 due to the deformation of the deformable portion 8 when the first portion 21 in the first route P1 is pulled.

Thus, as shown in FIG. 4A, when the second portion 22 in the second route P2 is pulled, the suture 2 is pulled toward the upper side at the other end side of the deformable portion 8. Therefore, a pressing force that causes the deformable portion 8 to be deformed toward the lower side is not applied to the deformable portion 8 from the suture 2 and the suture 2 is moved with respect to the base 7 and the deformable portion 8 in accordance with the pulling force. In other words, as a result of the free end portion 2b being pulled, the suture 2 is moved with respect to the second anchor 12 away from the first anchor 11. As the suture 2 is moved with respect to the second anchor 12, a portion of the suture 2 between the anchors 11 and 12 becomes shorter and shifts into a tensioned state from a relaxed state.

On the other hand, as indicated by the arrow in FIG. 4B, when the first portion 21 in the first route P1 is pulled, the suture 2 is pulled toward a lower side at the other end side of the deformable portion 8. Therefore, the pressing force that causes the deformable portion 8 to be deformed toward the lower side is applied to the deformable portion 8 from the suture 2, the other end portion of the deformable portion 8 is pressed toward the thin portion 71 of the base 7, and the suture 2 is held between the thin portion 71 and the other end portion of the deformable portion 8. The held suture 2 cannot be moved with respect to the suture anchor 12 regardless of the pulling force and is secured with respect to the suture anchor 12. With an increase in the pulling force, the tensile force increases and the deformable portion 8 is pressed against the thin portion 71 with a greater force; therefore, the securing force with respect to the suture 2 increases.

Guide grooves 13 and 14 for preventing the suture 2 from being moved in transverse directions of the base 7 and the deformable portion 8 may be formed in the side surface 72b on the one end side of the base 7 and a side surface on the other end side of the deformable portion 8. The guide groove 13 extends over the entire length of the base 7 in the thickness direction thereof at a center of the transverse direction of the base 7 and accommodates the suture 2 in the radial direction. The guide groove 14 extends over the entire length of the deformable portion 8 in the thickness direction thereof at a center of the transverse direction of the deformable portion 8 and accommodates the suture 2 in the radial direction. With this configuration, when a tensile force is applied to the suture 2, the suture 2 is prevented from slipping along a surface of the base 7 or the deformable portion 8 in the transverse direction and falling off from the suture anchor 12, and thus, it is possible to hold the suture 2 at an appropriate position with respect to the base 7 and the deformable portion 8.

Next, a laceration repair method employing the laceration repair device 1 will be described with reference to FIGS. 7-10B.

Figure 8:
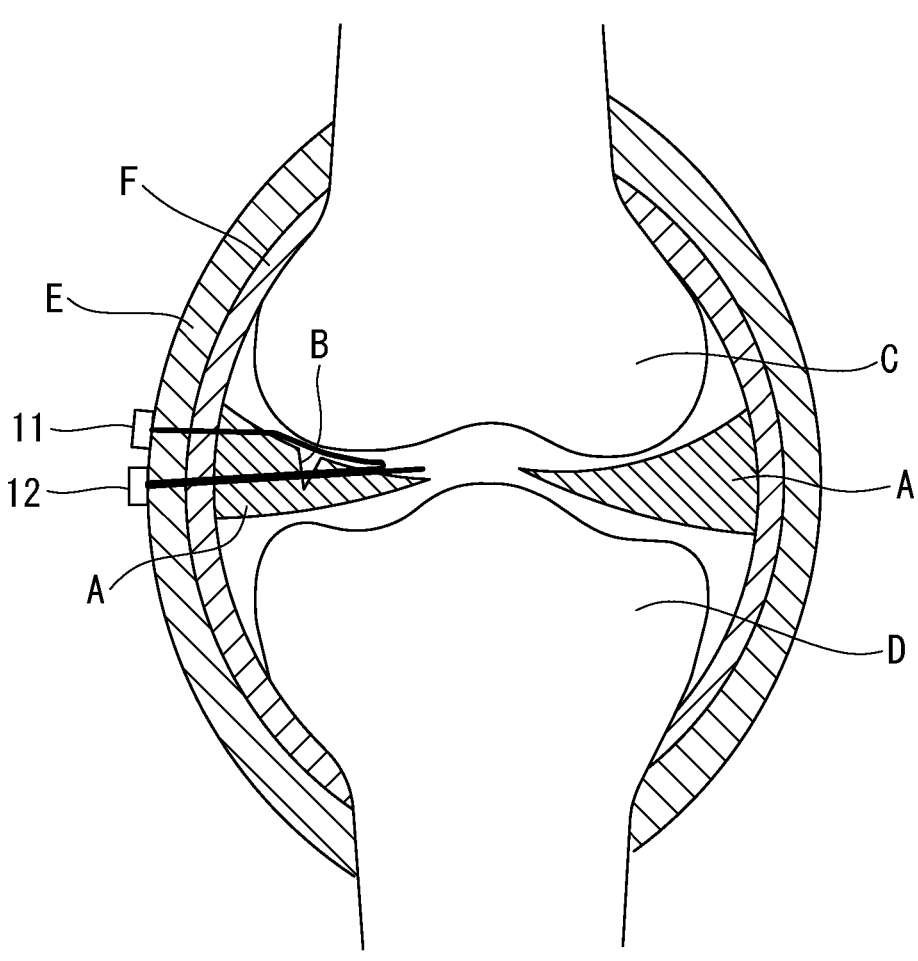
FIG. 8 is a diagram for explaining the arrangements of knee joint structures, the first anchor, and the second anchor.
Figure 9A:
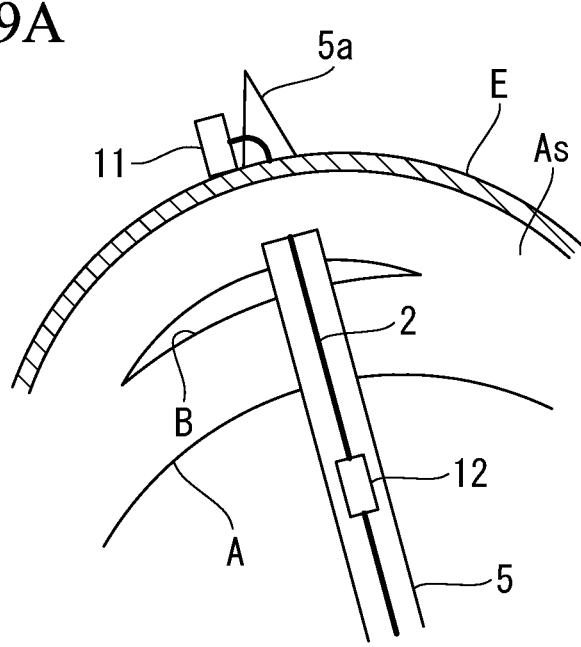
FIG. 9A is a diagram for explaining a step for disposing the first anchor in the method in FIG. 7.
Figure 9B:
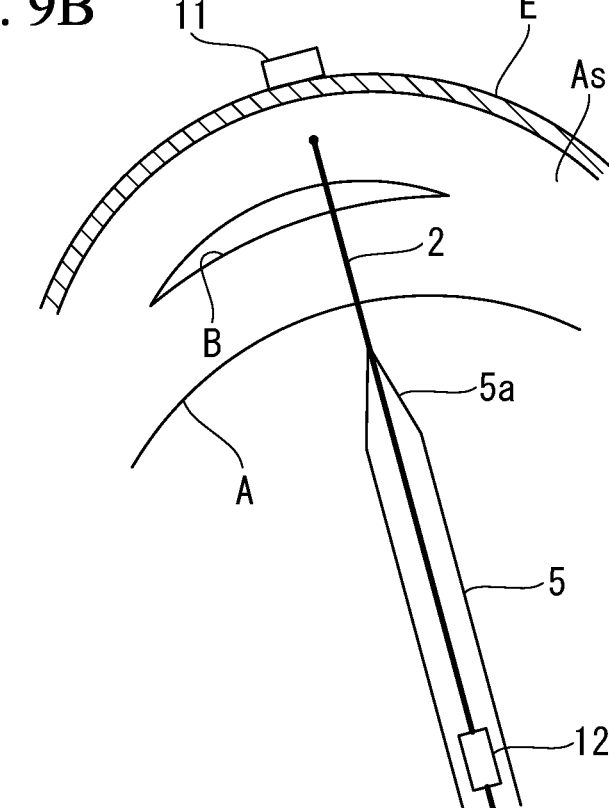
FIG. 9B is a diagram for explaining the step for disposing the first anchor in the method in FIG. 7.
Figure 9C:
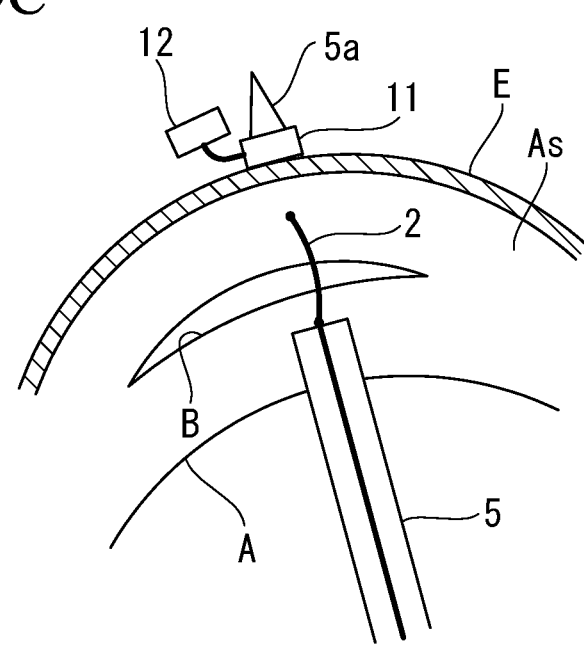
FIG. 9C is a diagram for explaining a step for disposing the second anchor in the method in FIG. 7.
Figure 9D:
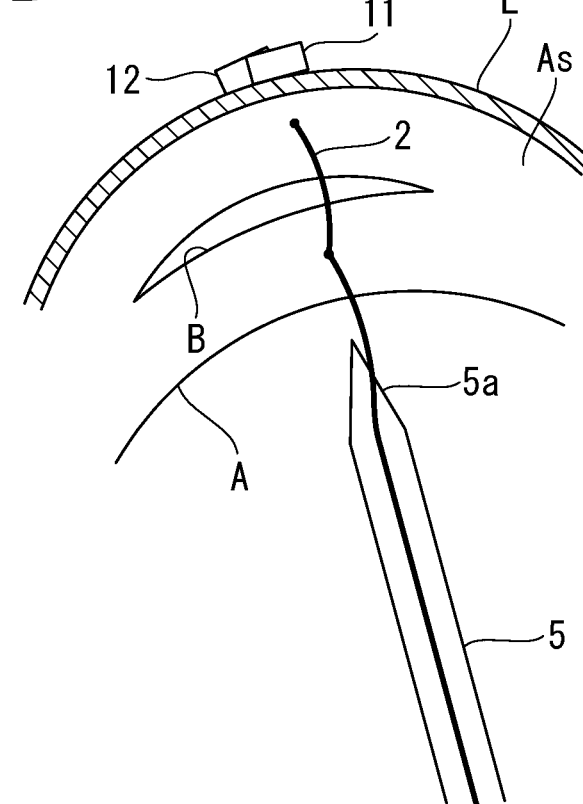
FIG. 9D is a diagram for explaining the step for disposing the second anchor in the method in FIG. 7.
Figure 9E:
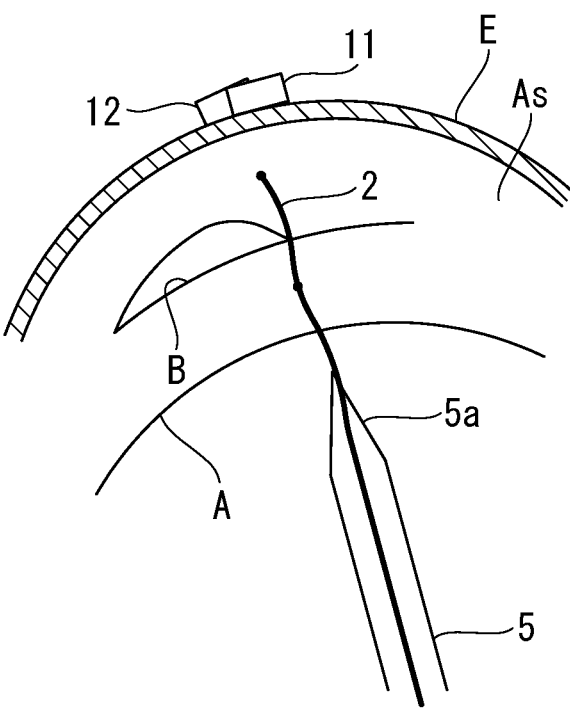
FIG. 9E is a diagram for explaining a step for pulling a free-end portion of the suture in the method in FIG. 7.
Figure 9F:
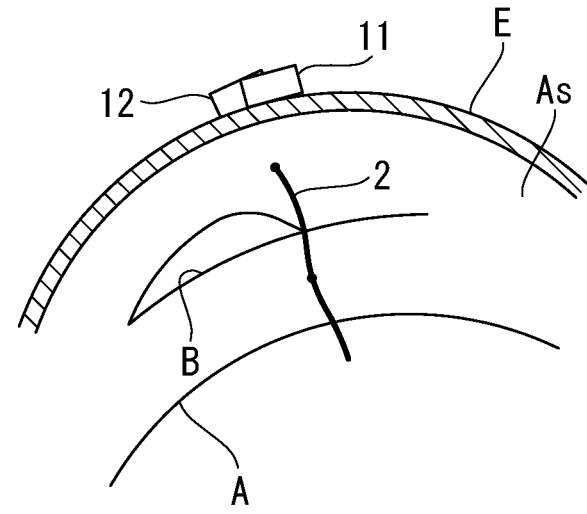
FIG. 9F is a diagram for explaining a step for cutting the suture in the method in FIG. 7.
Figure 10A:
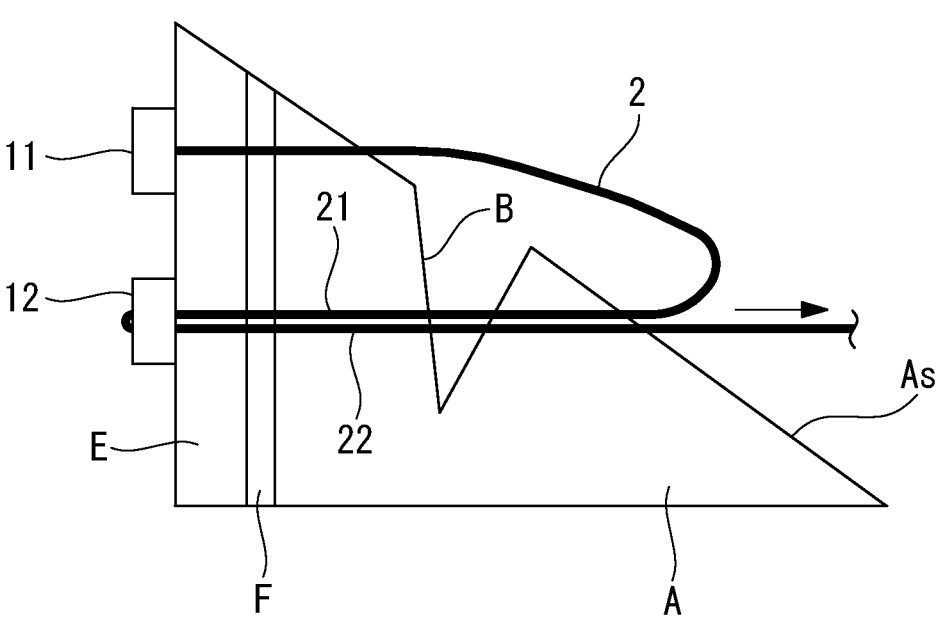
FIG. 10A is a longitudinal sectional view of a meniscus for explaining the arrangements of the first anchor, the second anchor, and the suture.
Figure 10B:
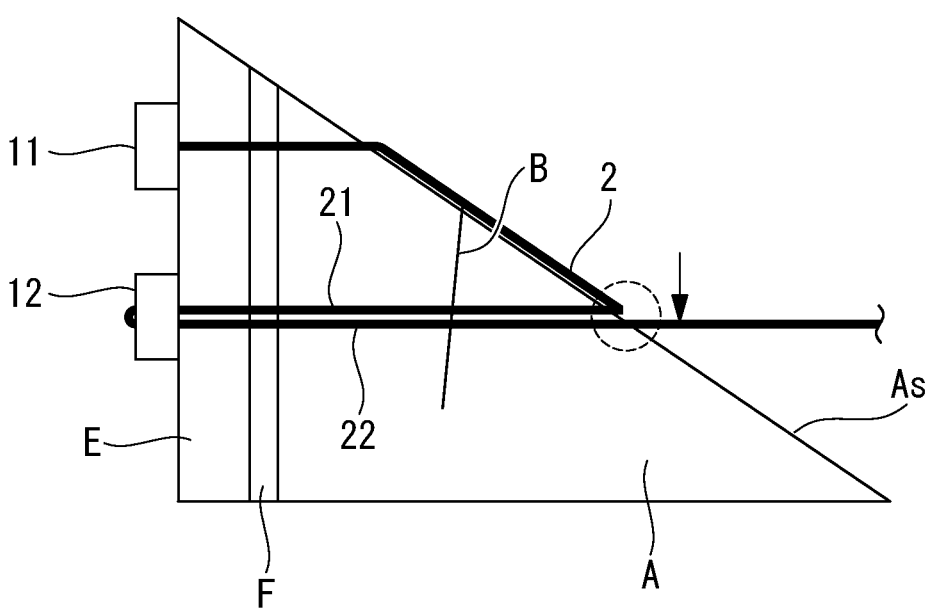
FIG. 10B is a longitudinal sectional view of the meniscus for explaining the arrangements of the first anchor, the second anchor, and the suture.

FIGS. 8-10B show, as an example, a case of repairing a laceration B of a meniscus A of a knee joint. As shown in FIG. 8, the meniscus A is crescent shaped or C-shaped soft tissue disposed between a joint surface of a femur C and a joint surface of a tibia D, an outer edge of the meniscus A is connected to a joint capsule E encasing the knee joint. Reference sign F indicates a synovium. FIGS. 8-9F show, as an example of the laceration B, a longitudinal fracture in which the meniscus A is torn in a longitudinal direction. FIGS. 9A-9F are diagrams in which the meniscus A is viewed from the femur C side and the synovium F is omitted. FIGS. 10A and 10B are longitudinal sectional view of the meniscus A in the laceration B.

Figure 7:
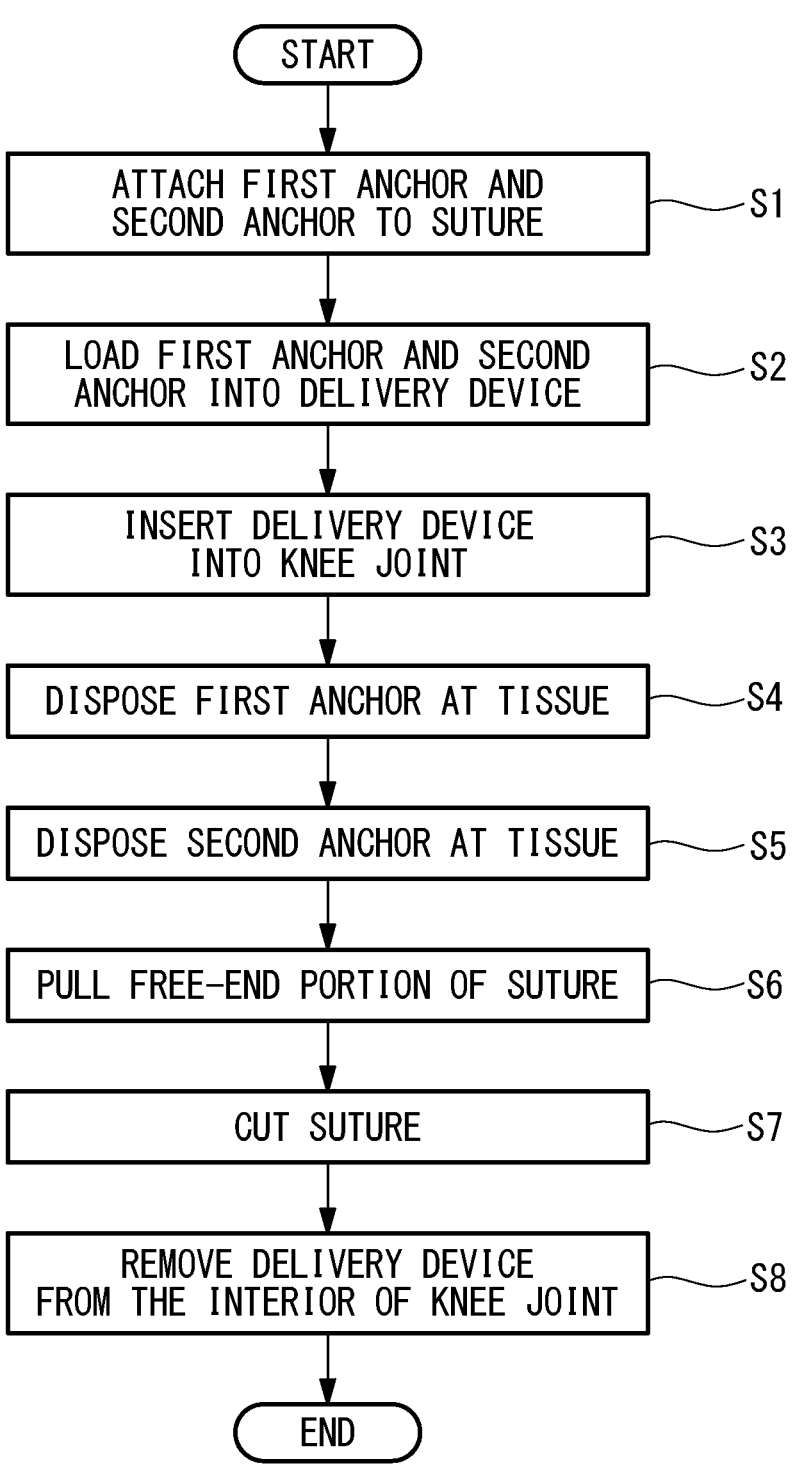
FIG. 7 is a flowchart showing a laceration repair method employing the laceration repair device in FIG. 1.

As shown in FIG. 7, the laceration repair method includes first step S1 to eighth step S8.

In first step S1, the first anchor 11 and the second anchor 12 are attached to the suture 2 by means of the above-described method. Next, in second step S2, the anchors 11 and 12 attached to the suture 2 are loaded into the needle 5 of the delivery device 3. As described above, in the case in which the laceration repair device 1 is provided to the user in the state in which the anchors 11 and 12 are loaded to the delivery device 3, the user does not need to perform steps S1 and S2. Therefore, steps S1 and S2 may be omitted.

Prior to third step S3, an arthroscope is inserted into the knee joint. As needed, a liquid is injected into the knee joint in order to expand the knee joint, and the size of the laceration B is measured.

Next, in third step S3, the delivery device 3 is inserted into the knee joint.

Next, in fourth step S4, the first anchor 11 is disposed at the joint capsule (tissue) E. Specifically, as shown in FIG. 9A, the meniscus A is pierced with the needle 5 radially outside the laceration B and the needle 5 is made to pass through the meniscus A until the needle tip 5a protrudes from an outer surface of the joint capsule E. Next, the first anchor 11 is pushed out from the needle tip 5a and the first anchor 11 is disposed on the outer surface of the joint capsule E. Next, as shown in FIG. 9B, the delivery device 3 is pulled toward the proximal side and the needle 5 is removed from the meniscus A.

Next, in fifth step S5, the second anchor 12 is disposed at the joint capsule E. Specifically, as shown in FIG. 9C, the meniscus A is pierced with the needle 5 on radially inside the laceration B and the needle 5 is made to pass through the meniscus A, crossing the laceration B, until the needle tip 5a protrudes from the outer surface of the joint capsule E. Next, the second anchor 12 is pushed out from the needle tip 5a, and the second anchor 12 is disposed on the outer surface of the joint capsule E. Next, as shown in FIG. 9D, the delivery device 3 is pulled toward the proximal side, and the needle 5 is removed from the meniscus A.

As a result of performing fourth step S4 and fifth step S5, as shown in FIG. 10A, the portion of the suture 2 between the first anchor 11 and the second anchor 12 crosses the laceration B on a surface As of the meniscus A.

Next, in sixth step S6, as indicated by the arrow in FIG. 10A, the free end portion 2b of the suture 2 is pulled. As the free end portion 2b is pulled, the portion of the suture 2 between the first anchor 11 and the second anchor 12 gradually becomes shorter and the laceration B is closed, as shown in FIGS. 9E and 10B.

Next, in seventh step S7, as shown in FIG. 9F, the suture 2 is cut by using an arbitrary instrument inserted into the knee joint. The arrow in FIG. 10B indicates the position at which the suture 2 is cut. As shown in FIG. 10B, after cutting the suture 2, only the thin, flexible suture 2 remains on the surface As on the femur C side of the meniscus A.

Next, in eighth step S8, the delivery device 3 is pulled toward the proximal side and the delivery device 3 is removed from the knee joint.

After the laceration B is closed as a result of pulling the free end portion 2b, there are cases in which the suture 2 is pulled in the direction in which the laceration B opens, in other words, there are cases in which the first portion 21 in the first route P1 is pulled. With the suture anchor 12 of this embodiment, when the suture 2 is pulled in the direction in which the laceration B opens, the suture 2 is secured with respect to the suture anchor 12 by the deformable portion 8 being deformed due to the tensile force of the suture 2 and the movement of the suture 2 in the direction in which the laceration B opens is prevented. Specifically, after closing the laceration B once by pulling the free end portion 2b, loosening of the suture 2 is prevented by the deformable portion 8 and the tensile force of the suture 2 between the first anchor 11 and the second anchor 12 is maintained. Therefore, although a structure, such as a slip knot, for preventing loosening of the suture 2 has conventionally been necessary at the position indicated by the broken-line circle in FIG. 10B, such a structure is not required in this embodiment. Accordingly, it is possible to complete suturing without leaving a protruding object, such as a knot, for preventing loosening of the suture 2 on the surface As of soft tissue A after suturing. In the case in which the soft tissue A is a meniscus, because a protruding object does not remain on the femur C-side surface As, which is a sliding surface of the knee joint, it is possible to prevent an influence on sliding of the joint.

In addition, because a knot that has conventionally been necessary is not required, there is an advantage in that it is possible to simplify the procedures. FIG. 17 shows a comparative example of the laceration repair method according to this embodiment, which is a laceration repair method for the case in which a slip knot is formed in the suture 2.

In the comparative example, step S2' for forming a knot in the suture 2 after attaching the suture 2 to two conventional anchors is necessary. In addition, step S7' for moving the knot to a surface of the soft tissue by pulling the suture 2 after disposing the second anchor is necessary. In this case, the knot is disposed at the position indicated by the broken-line circle in FIG. 10B. In this embodiment, these steps S2' and S7' are not required.

In the case in which the rigidity of the base 7 is low, not only the deformable portion 8 but also the base 7 could be deformed due to the tensile force of the suture 2. In order to prevent the deformation of the base 7, the base 7 may have a greater rigidity as compared with the deformable portion 8.

Figure 11A:
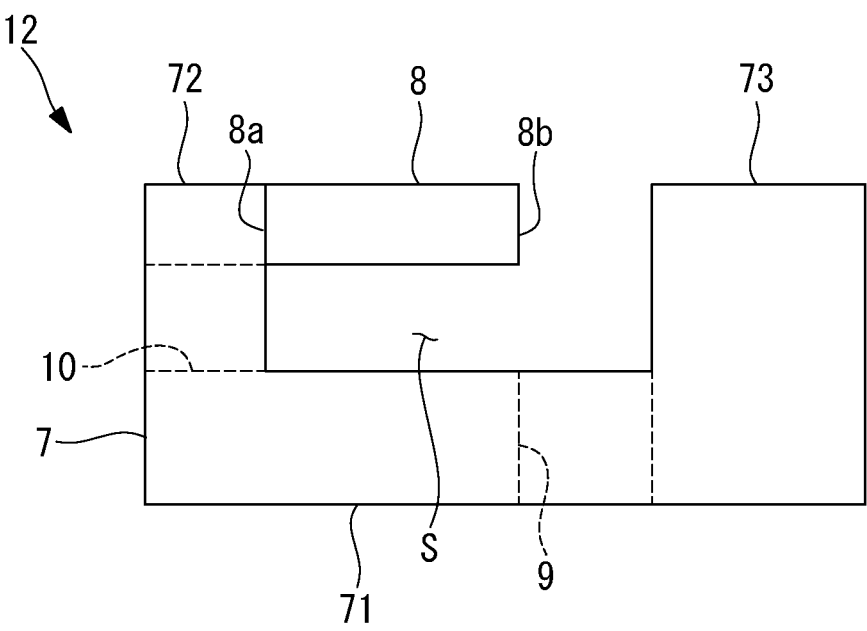
FIG. 11A is a side view of a modification of the second anchor in which the rigidity of a base is enhanced.
Figure 11B:
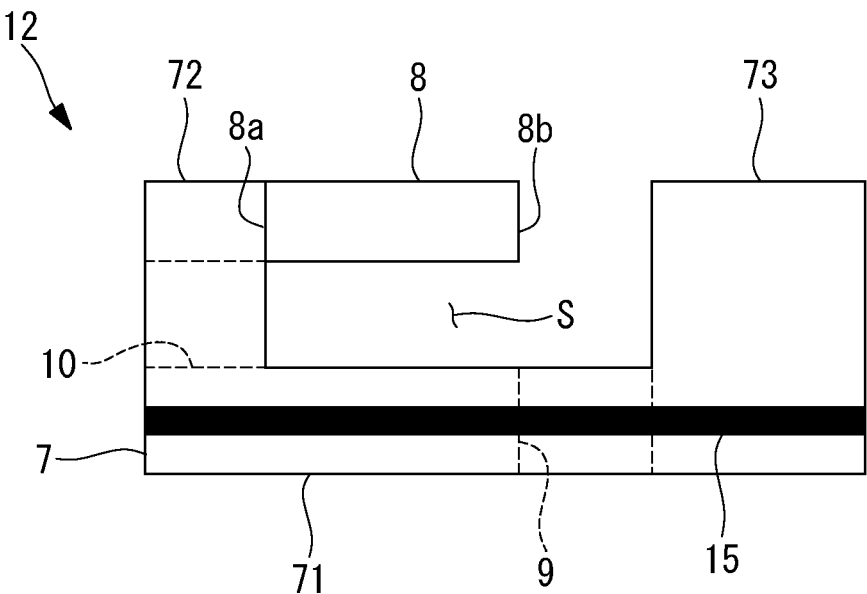
FIG. 11B is a side view of another modification of the second anchor in which the rigidity of the base is enhanced.

FIGS. 11A and 11B show an example of the suture anchor 12 in which the rigidity of the base 7 is enhanced. In FIG. 11A, the thickness of the base 7 is increased and the thin portion 71 has a greater thickness than the deformable portion 8. In FIG. 11B, a high-rigidity material 15 is incorporated into the base 7 by means of integral molding. The high-rigidity material 15 is formed from, for example, a meatal such as a titanium alloy.

In this embodiment, a structure for increasing the securing force with respect to the suture 2 may be provided in at least one of the base 7 and the deformable portion 8. FIGS. 12-15 show examples of the structure for increasing the securing force.

Figure 12:
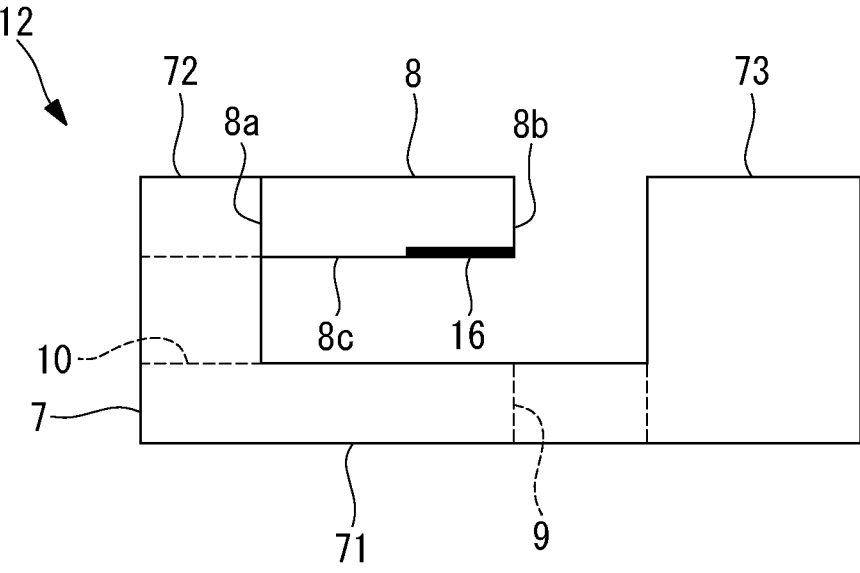
FIG. 12 is a side view of a modification of the second anchor subjected to friction increasing treatment.

Two or more of a friction increasing treatment 16 in FIG. 12, a groove 17 in FIGS. 13A-14B, and protrusions 18 in FIG. 15 may be provided in the suture anchor 12.

In FIG. 12, the friction increasing treatment 16 is applied to a bottom surface 8c of the deformable portion 8. One example of the friction increasing treatment 16 is a treatment for forming a rough surface in the bottom surface 8c by forming a plurality of depressions or a plurality of protrusions on the bottom surface 8c. The deformed deformable portion 8 is in firm contact with the suture 2 at the other end portion. Therefore, it is most effective to apply the friction increasing treatment 16 to the bottom surface 8c at the other end portion of the deformable portion 8. Due to the friction increasing treatment 16, it is possible to increase the frictional force between the bottom surface 8c of the deformed deformable portion 8 and the suture 2.

Figure 13A:
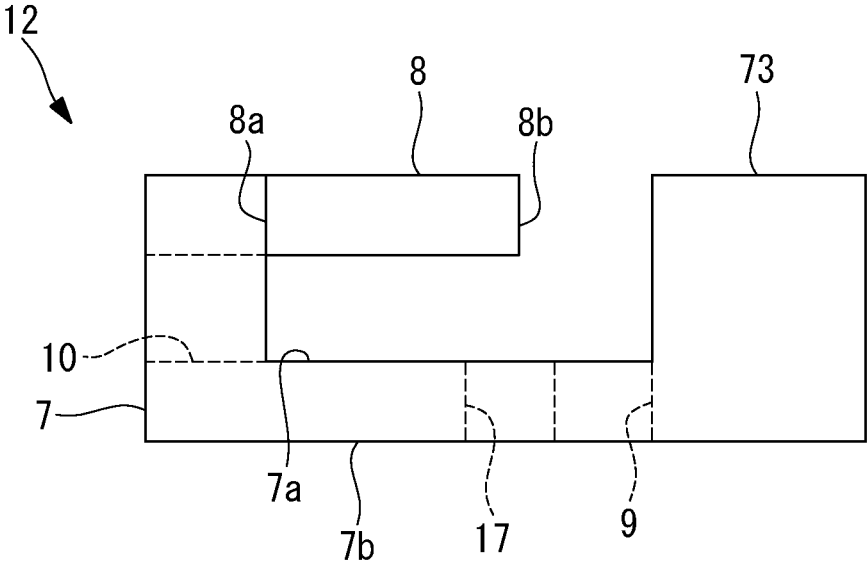
FIG. 13A is a side view of another modification of the second anchor provided with a groove in an inner surface of a first passage.
Figure 13B:
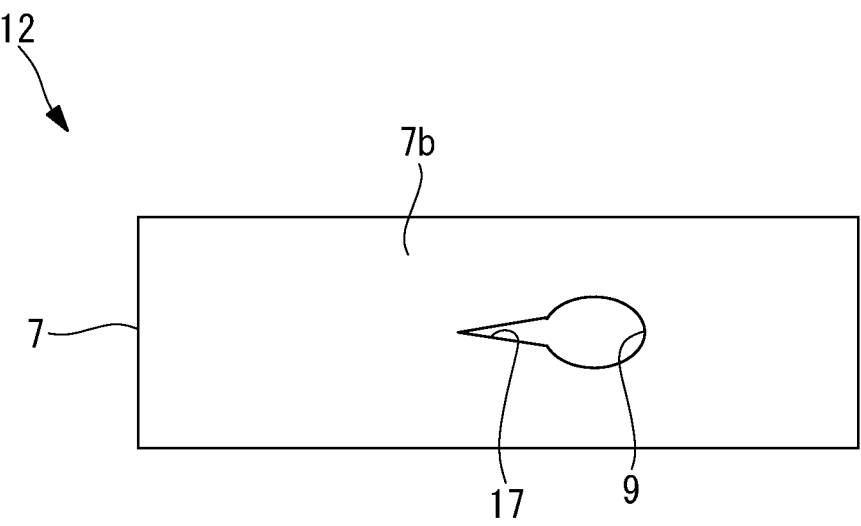
FIG. 13B is a bottom view of the second anchor in FIG. 13A.
Figure 13C:
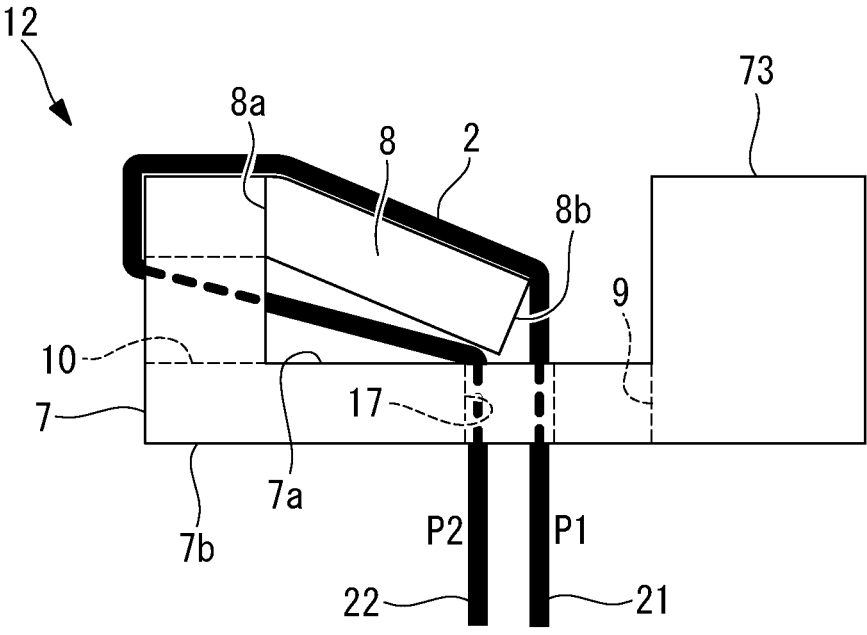
FIG. 13C is a side view of the second anchor in FIG. 13A in a state in which the deformable portion is deformed.

In FIGS. 13A-13C, the groove 17 is formed in an inner surface of the first passage 9. The groove 17 is formed in a region on the one end side in the inner surface of the first passage 9 and extends toward the bottom surface 7b from the top surface 7a. It is preferable that at least a portion of the groove 17 have a diameter that is smaller than the diameter of the suture 2. In the illustrated example, the groove 17 has a V-shape in which the width thereof gradually decreases toward the one end side.

When an additional tensile force is applied to the suture 2 in the state in which the deformed deformable portion 8 is holding down the suture 2 in the second route P2, the two portions of the suture 2 in the first passage 9 enter the groove 17 and friction is generated between an inner surface of the groove 17 and the suture 2. Due to this friction, the securing force with respect to the suture 2 increases.

As shown in FIGS. 14A and 14B, the first passage 9 may have two holes 91 and 92 that are arrayed in the longitudinal direction of the base 7, and the groove 17 may be formed in an inner surface of the hole 91 on the other end side. The first portion 21 in the first route P1 passes through the hole 91, and the second portion 22 in the second route P2 passes through the hole 92 on the one end side.

With this configuration, when the first portion 21 is pulled, the second portion 22 passing through the hole 92 is secured by being held between the thin portion 71 and the deformed deformable portion 8, and the first portion 21 passing through the hole 91 is secured by getting into the groove 17.

In FIG. 15, the bottom surface 8c of the deformable portion 8 is provided with one or more protrusions 18 that protrude toward the lower side. As with the friction increasing treatment 16, it is preferable that the protrusions 18 be provided on the bottom surface 8c of the other end portion of the deformable portion 8. As a result of the protrusions 18 being pressed against the suture 2 when the deformable portion 8 is deformed, the securing force with respect to the suture 2 increases.

In the above-described embodiment, the orientations and the positions of the first passage 9 and the second passage 10 may be changed, so long as it is possible to wind the suture 2 around the deformable portion 8 so that the suture 2 extends from the first passage 9 and returns to the first passage 9 via the other end side, the upper side, and the one end side of the deformable portion 8, the second passage 10, and the space S.

For example, the entire first passage 9 may be formed on the one end side with respect to the free end 8b. The second passage 10 may extend through only the thick portion 72 in the longitudinal direction of the base 7, as shown in FIGS. 11A-15, or the second passage 10 may extend through only the thin portion 71 of the base 7 in the thickness direction. Alternatively, the second passage 10 may be an L-shaped passage that extends through the thick portion 72 from the side surface 72a to the top surface 7a.

FIGS. 16A-16C show a modification of the suture anchor 12. In the suture anchor 12 in FIGS. 16A-16C, the second passage 10 is a hole that extends through the thick portion 72 of the base 7 in the thickness direction and that opens in the top surface 7a and the bottom surface 7b of the thick portion 72 and opens into the space S. It is preferable that the second passage 10 also extend through the one end portion of the thin portion 71 in the thickness direction and form a large opening in the bottom surface 7b so that it is possible to make the suture 2 easily pass into the second passage 10 from the lower side. With such a second passage 10 also, it is possible to guide the suture 2 to the space S from the one end side of the secured end 8a. In addition, it is possible to reliably prevent the suture 2 from falling off from the base 7.

In this embodiment, the base 7 has the thin portion 71 and the thick portion 72 and the deformable portion 8 is disposed so as to be parallel to the thin portion 71; however, so long as the secured end 8a is secured to the base 7 and the free end 8b is disposed so as to be separated by the space S from the base 7, it is possible to change the shape of the base 7 and the arrangement of the deformable portion 8 with respect to the base 7. For example, the base 7 may be a flat plate having the flat top surface 7a and bottom surface 7b and the deformable portion 8 may be inclined upward toward the free end 8b from the secured end 8a with respect to the base 7.

Although this embodiment has been described in terms of a case in which the suture anchor 12 and the laceration repair device 1 are used to repair a laceration of a meniscus, tissue to which the suture anchor 12 and the laceration repair device 1 are applied is not limited to a meniscus and may be other soft tissue, such as a muscle, a ligament, and cartilage.

In a conventional art, a slip knot that prevents the movement of the suture in the direction in which the wound opens is necessary in order to prevent the wound from opening as a result of the suture becoming loosened after closing the wound. Therefore, time and effort are required to form the knot. In addition, after repairing the wound, the knot remains on the tissue surface as a protruding object. In the case in which the tissue is a meniscus, the knot is disposed on a sliding surface of the joint; therefore, the knot may affect sliding of the joint.

The following aspects have been conceived in light of the above-described circumstances, and an object thereof is to provide a suture anchor and a device that are capable of preventing loosening of a suture without having to leave a protruding object such as a knot on a tissue surface.

An aspect of the present invention is a suture anchor including: a plate-like base that has an upper side and a lower side in a thickness direction of the base and that has one end and the other end in a direction intersecting the thickness direction; a deformable portion disposed at an upper side of the base, at least a side of the other end of the deformable portion being disposed so as to be separated by a space from the base; and a first passage and a second passage each formed in the base to allow a suture to pass therethrough, wherein the deformable portion is a cantilever state having a fixed end, which is disposed at a side of the one end and fixed to the base, and a free end, which is disposed at a side of the other end, and the deformable portion is deformable in a direction in which the free end approaches the base, the first passage communicates the upper side and the lower side of the base, the second passage is formed on a side of the one end relative to the free end and the first passage and communicates the space and a side of the one end of the fixed end, and the deformable portion is deformed due to a tensile force applied to the suture, which extends from the first passage and returns to the first passage via a side of the other end relative to the deformable portion, an opposite side of the deformable portion when seen from the base, a side of the one end relative to the deformable portion, the second passage, and the space, and to hold the suture between the deformable portion and the base.

The suture anchor of this aspect is attached to the suture by winding the suture to surround the deformable portion by making the suture sequentially pass through the first passage, the second passage, and the first passage. Specifically, the suture passes through the first passage from the lower side of the base to the upper side, passes through the second passage from the side of the one end of the deformable portion to the space via the side of the other end of the deformable portion, the side of the deformable portion opposite to the base, and side of the one end of the deformable portion, and passes through the first passage from the upper side of the base to the lower side. As a result of a tensile force being applied to the suture that is wound around the deformable portion in the above-described way, the cantilever sate deformable portion is deformed in the direction in which the free end approaches the base, the suture disposed in the space is held between the base and the deformed deformable portion, and thus, the suture is secured with respect to the suture anchor.

As described above, with the suture anchor of this aspect, the suture anchor itself applies the securing force with respect to the suture due to the tensile force of the suture; therefore, a protruding object, such as a knot, for preventing unintentional movement of the suture with respect to the suture anchor is not required. Accordingly, it is possible to prevent loosening of the suture without having to leave a protruding object on a tissue surface.

In the above-described aspect, the first passage may have a first hole that extends through the base, and the second passage may have a second hole that extends through the base. The base may have a thin portion that faces the deformable portion in the thickness direction and a thick portion that is provided on the one end side of the thin portion, and the second hole may extend through the thick portion in a longitudinal direction of the base.

With this configuration, it is possible to provide the first passage and the second passage by means of simple processing for simply forming the holes extending through the base, and thus, it is possible to simplify the configuration of the base.

In the above-described aspect, the first hole may be formed on a side of the other end with respect to the free end, and the second hole may be formed on a side of the one end with respect to the free end.

As a result of forming the first hole on the side of the other end with respect to the free end, it is possible to make the suture easily pass through the first hole without being interfered by the deformable portion. In addition, as a result of forming the first hole and the second hole on either side of the free end, it is possible to hold a portion of the suture extending from the second hole to the first hole between the deformed deformable portion and the base.

In the above-described aspect, a friction increasing treatment may be applied to a bottom surface of a base side of the deformable portion.

When the deformable portion is deformed, the bottom surface of the deformable portion comes into contact with the suture. The friction between the deformed deformable portion and the suture increases due to the friction increasing treatment on the surface of the deformable portion, and thus, it is possible to increase the securing force with respect to the suture.

In the above-described aspect, a groove that extends in the thickness direction may be provided in a region on a side of the one end in an inner surface of the first hole.

With this configuration, when a tensile force is applied to the suture, the suture in the first hole is pulled toward the side of the one end and gets into the groove, and thus, friction is generated between the suture and an inner surface of the groove. Accordingly, it is possible to increase the securing force with respect to the suture.

In the above-described aspect, a protrusion may be provided in a bottom surface of a base side of the deformable portion.

With this configuration, as a result of the protrusion being pressed against the suture when the deformable portion is deformed, it is possible to increase the securing force with respect to the suture.

Another aspect of the present invention is a laceration repair device including: a suture; a first anchor attached to the suture; any one of the suture anchors described above, which serves as a second anchor attached to the suture, and a delivery device that has a hollow needle and that is capable of loading the first anchor and the second anchor in an interior of the needle, wherein the suture is attached to the second anchor so as to be movable relative to the second anchor in a direction away from the first anchor.

In the above-described another aspect, as a result of pulling a portion of the suture on the first anchor side, which extends toward the first anchor from the second anchor, a tensile force may be generated in the suture and the deformable portion may be deformed.

In the above-described other aspect, the second anchor may be attached to the suture at a position between a free-end portion of the suture and the first anchor, and, a portion of two portions of the suture that pass through the first passage, which is one at a side of the first anchor, extends from the first passage to the opposite side of the deformable portion when seen from the base via the side of the other end of the deformable portion.

With this configuration, when a pulling force toward the first anchor side acts on a portion of the suture extending from the second anchor to the first anchor, a tensile force is generated in the suture, the suture is held by the deformed deformable portion, and the movement of the suture with respect to the second anchor is prevented. Thus, it is possible to prevent the suture from moving with respect to the second anchor in a direction in which the length of the portion of the suture between the second anchor and the first anchor increases.

The above aspects afford an advantage in that it is possible to prevent loosening of a suture without having to leave a protruding object such as a knot on a tissue surface.

REFERENCE SIGNS LIST 1 laceration repair device
11 first anchor
12 second anchor, suture anchor
2 suture
3 delivery device
5 needle
5a needle tip
7 base
7a top surface
7b bottom surface
8 deformable portion
8a secured end
8b free end
8c bottom surface
9 first passage, first hole
10 second passage, second hole
16 friction increasing treatment
17 groove
18 protrusion

The invention claimed is:

1. A suture anchor comprising:
a plate-like base that has an upper side and a lower side in a thickness direction of the base and that has a first end and a second end in an extending direction intersecting the thickness direction;
a deformable portion disposed at an upper side of the base, the deformable portion including a fixed end portion fixed to the base, the deformable portion extending along the base and having a free end which is closer to the second end than the fixed end portion, the free end being disposed so as to be separated by a space from the base; and
a first passage and a second passage each formed in the base to allow a suture to pass therethrough, wherein the deformable portion is deformable in a direction in which the free end approaches the base, wherein the first passage communicates the upper side and the lower side of the base, wherein the second passage is formed at a position closer to the first end than the first passage and communicates between the space and an opposite side of the fixed end portion when seen from the space, and wherein the deformable portion is deformed due to a tensile force applied to the suture, which extends from the first passage and returns to the first passage via an opposite side of the free end of the deformable portion when seen from the base, the second passage, and the space, and to hold the suture between the deformable portion and the base.

2. The suture anchor according to claim 1, wherein the first passage has a first hole that extends through the base.

3. The suture anchor according to claim 2, wherein the second passage has a second hole that extends through the base.

4. The suture anchor according to claim 3, wherein at least part of the first hole is formed at a position farther from the fixed end portion than the free end in the extending direction, and wherein the second hole is formed at a position closer to the fixed end portion than the free end.

5. The suture anchor according to claim 4, wherein a friction increasing treatment is applied to a bottom surface of a base side of the deformable portion.

6. The suture anchor according to claim 4, wherein a groove that extends in the thickness direction is provided in a region, which is close to the first end, of an inner surface of the first hole.

7. The suture anchor according to claim 4, wherein a protrusion is provided in a bottom surface of a base side of the deformable portion.

8. The suture anchor according to claim 3, wherein the base has a thin portion that faces the deformable portion in the thickness direction and a thick portion that is provided at a position closer to the fixed end portion than the thin portion, and wherein the second hole extends through the thick portion in the extending direction.

9. A laceration repair device comprising:
a suture;
a first anchor attached to the suture;
a suture anchor which serves as a second anchor attached to the suture; and
a delivery device that has a hollow needle and that is capable of loading the first anchor and the second anchor in an interior of the needle, wherein the suture is attached to the second anchor so as to be movable relative to the second anchor in a direction away from the first anchor, and wherein the suture anchor comprises:
a plate-like base that has an upper side and a lower side in a thickness direction of the base and that has a first end and a second the other end in an extending direction intersecting the thickness direction;
a deformable portion disposed at an upper side of the base, the deformable portion including a fixed end portion fixed to the base, the deformable portion extending along the base and having a free end which is closer to the second end than the fixed end portion, the free end being disposed so as to be separated by a space from the base; and
a first passage and a second passage each formed in the base to allow a suture to pass therethrough, wherein the deformable portion is deformable in a direction in which the free end approaches the base, wherein the first passage communicates the upper side and the lower side of the base, wherein the second passage is formed at a position closer to the first end than the first passage and communicates between the space and an opposite side of the fixed end portion when seen from the space, and wherein the deformable portion is deformed due to a tensile force applied to the suture, which extends from the first passage and returns to the first passage via an opposite side of the free end of the deformable portion when seen from the base, the second passage, and the space, and to hold the suture between the deformable portion and the base.

10. The laceration repair device according to claim 9, wherein, as a result of pulling a portion of the suture on a side of the first anchor, which extends to the first anchor from the second anchor, a tensile force is generated in the suture and the deformable portion is deformed.

11. The laceration repair device according to claim 10, wherein the second anchor is attached to the suture at a position between a free-end portion of the suture and the first anchor, and wherein a closer one of two portions of the suture that pass through the first passage extends from the first passage to the second passage via the opposite side of the free end of the deformable portion when seen from the base.

* * * * *